(12) United States Patent
Hasan

(10) Patent No.: US 8,742,754 B2
(45) Date of Patent: Jun. 3, 2014

(54) METHOD AND SYSTEM FOR DIFFUSION TENSOR IMAGING

(75) Inventor: Khader M. Hasan, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 476 days.

(21) Appl. No.: 13/028,286

(22) Filed: Feb. 16, 2011

(65) Prior Publication Data

US 2011/0199084 A1  Aug. 18, 2011

Related U.S. Application Data

(60) Provisional application No. 61/304,986, filed on Feb. 16, 2010.

(51) Int. Cl.
*G01V 3/00* (2006.01)

(52) U.S. Cl.
USPC .......................................................... 324/307

(58) Field of Classification Search
None
See application file for complete search history.

(56) References Cited

U.S. PATENT DOCUMENTS

| | | | | |
|---|---|---|---|---|
| 6,463,315 | B1 * | 10/2002 | Klingberg et al. | 600/410 |
| 7,602,180 | B2 * | 10/2009 | McGraw | 324/307 |
| 7,671,592 | B2 * | 3/2010 | Kabasawa | 324/309 |
| 7,672,790 | B2 * | 3/2010 | McGraw et al. | 702/19 |
| 8,170,305 | B2 * | 5/2012 | Laidlaw et al. | 382/128 |
| 8,452,373 | B2 * | 5/2013 | Wyrwicz et al. | 600/410 |

* cited by examiner

*Primary Examiner* — Dixomara Vargas
(74) *Attorney, Agent, or Firm* — Conley Rose, P.C.

(57) ABSTRACT

Methods and systems for displaying microstructural integrity and/or connectivity of a region of interest (ROI) in a patient are disclosed. Methods and systems for tissue segmentation and atlas-based tissue segmentation in ROI of a patient using diffusion MRI data are also described. A method for studying microstructural integrity and/or connectivity of a region of interest (ROI) in a patient includes acquiring, via an imaging system, diffusion magnetic resonance (MRI) data in the ROI by using an Icosahedral Diffusion Tensor Encoding Scheme (IDTES); computing, via the imaging system, mean diffusivity (MD) and fractional anisotropy (FA) by using logarithm-moment algorithm (LMA); and displaying, on a display, the microstructural integrity and/or connectivity of ROI based on the computed MD and FA. The diffusion MRI data includes diffusion-weighted imaging (DWI) data or diffusion tensor imaging (DTI) data. In some cases, displaying the microstructural integrity and/or connectivity of ROI takes place in real time.

20 Claims, 19 Drawing Sheets

METHOD AND SYSTEM FOR DIFFUSION TENSOR IMAGING

CROSS-REFERENCE TO RELATED APPLICATION

The present application claims priority to U.S. Provisional Patent Application No. 61/304,986, filed on Feb. 16, 2010; which is hereby incorporated herein by reference in its entirety.

STATEMENT REGARDING FEDERALLY SPONSORED RESEARCH OR DEVELOPMENT

This invention was made with U.S. Government support under Grant No. NIH R01 NS052505-04 awarded by the National Institutes of Health. The government has certain rights in the invention.

BACKGROUND

1. Technical Field

This disclosure generally relates to brain mapping utilizing magnetic resonance imaging (MRI). More particularly, this disclosure relates to diffusion tensor imaging (DTI) for real-time display of brain structures and regional segmentation of brain tissues.

2. Background

Magnetic Resonance Imaging (MRI), or nuclear magnetic resonance imaging, is a medical imaging technique most commonly used to visualize detailed internal structures in the body. MRI provides much greater contrast between the different soft tissues of the body than computed tomography (CT). Furthermore, unlike CT, MRI involves no ionizing radiation because it uses a powerful magnetic field to align protons, most commonly those of the hydrogen atoms of the water present in tissue. A radio frequency electromagnetic field is then briefly turned on, causing the protons to alter their alignment relative to the field. When this field is turned off the protons return to their original magnetization alignment. These alignment changes create signals which are detected by a scanner. Images can be created because the protons in different tissues return to their equilibrium state at different rates. By altering the parameters on the scanner this effect is used to create contrast between different types of body tissue. MRI is used to image every part of the body, and is particularly useful for neurological conditions, for disorders of the muscles and joints, for evaluating tumors, and for showing abnormalities in the heart and blood vessels. Magnetic resonance imaging (MRI) methods provide several tissue contrast mechanisms that can be used to assess the micro- and macrostructure of living tissue in both health and disease. Diffusion MRI is a method that produces in vivo images of biological tissues weighted with the local microstructural characteristics of water diffusion. There are two distinct forms of diffusion MRI, diffusion weighted MRI and diffusion tensor MRI.

In diffusion weighted imaging (DWI), each image voxel (three dimensional pixel) has an image intensity that reflects a single best measurement of the rate of water diffusion at that location. This measurement is more sensitive to early changes such as occur after a stroke than more traditional MRI measurements such as T1 or T2 relaxation rates. DWI is most applicable when the tissue of interest is dominated by isotropic water movement e.g. grey matter in the cerebral cortex and major brain nuclei—where the diffusion rate appears to be the same when measured along any axis. Traditionally, in diffusion-weighted imaging (DWI), three gradient-directions are applied, sufficient to estimate the trace of the diffusion tensor or 'average diffusivity', a putative measure of edema. Clinically, trace-weighted images have proven to be very useful to diagnose vascular strokes in the brain, by early detection (within a couple of minutes) of the hypoxic edema.

Diffusion tensor imaging (DTI) is a technique that enables the measurement of the restricted diffusion of water in tissue in order to produce neural tract images instead of using this data solely for the purpose of assigning contrast or colors to pixels in a cross sectional image. It also provides useful structural information about muscle—including heart muscle, as well as other tissues such as the prostate. DTI is important when a tissue—such as the neural axons of white matter in the brain or muscle fibers in the heart—has an internal fibrous structure analogous to the anisotropy of some crystals. Water will then diffuse more rapidly in the direction aligned with the internal structure, and more slowly as it moves perpendicular to the preferred direction. This also means that the measured rate of diffusion will differ depending on the direction from which an observer is looking. In DTI, each voxel therefore has one or more pairs of parameters: a rate of diffusion and a preferred direction of diffusion, described in terms of three dimensional space, for which that parameter is valid. The properties of each voxel of a single DTI image is usually calculated by vector or tensor math from six or more different diffusion weighted acquisitions, each obtained with a different orientation of the diffusion sensitizing gradients. In some methods, hundreds of measurements—each making up a complete image—are made to generate a single resulting calculated image data set. The higher information content of a DTI voxel makes it extremely sensitive to subtle pathology in the brain. In addition the directional information can be exploited at a higher level of structure to select and follow neural tracts through the brain—a process called tractography.

More extended diffusion tensor imaging (DTI) scans derive neural tract directional information from the data using 3D or multidimensional vector algorithms based on three, six, or more gradient directions, sufficient to compute the diffusion tensor. The diffusion model is a rather simple model of the diffusion process, assuming homogeneity and linearity of the diffusion within each image voxel. From the diffusion tensor, diffusion anisotropy measures such as the fractional anisotropy (FA) can be computed. Moreover, the principal direction of the diffusion tensor can be used to infer the white-matter connectivity of the brain (i.e. tractography; trying to see which part of the brain is connected to which other part). Recently, more advanced models of the diffusion process have been proposed that aim to overcome the weaknesses of the diffusion tensor model. Amongst others, these include q-space imaging and generalized diffusion tensor imaging.

There are several applications for bran analysis that can benefit from the availability of robust methods for estimating cortical and subcortical gray matter (GM) volume and their corresponding quantitative relaxation or diffusion tensor metrics (Fjell A M, Westlye L T, Greve D N, Fischl B, Benner T, van der Kouwe A J, Salat D, Bjørnerud A, Due-Tønnessen P, Walhovd K B (2008): NeuroImage 42:1654-1668; Hasan K M, Kamali A, Kramer L A (2009a). Mapping the human brain white matter tracts relative to cortical and deep gray matter using diffusion tensor imaging at high spatial resolution. Magn Reson Imaging (doi: 10.1016/j.mri.2008.10.007); Lawes I N, Barrick T R, Murugam V, Spierings N, Evans D R, Song M, Clark C A (2008): Atlas-based segmentation of white matter tracts of the human brain using diffusion tensor tractography and comparison with classical dissection. NeuroImage 39:62-79; Mabbott D J, Noseworthy M, Bouffet E, Laughlin S, Rockel C (2006): White matter growth as a mechanism of cognitive development in children. NeuroImage 33:936-946; Makris N, Papadimitriou G M, Sorg S, Kennedy D N, Caviness V S, Pandya D N (2007): The occipitofrontal fascicle in humans: a quantitative, in vivo, DT-MRI study. NeuroImage 37:1100-1111; Wakana S, Jiang H, Nagae-Poetscher L M, van Zijl P C, Mori S (2004): Fiber tract-based atlas of human white matter anatomy. Radiology 23:77-87).

In general, current MRI methods for tissue volume assessment use high spatial resolution T1-weighted, or multi-modal T2-weighted, fluid-attenuated and proton density volumes for regional tissue segmentation. Tissue segmentation using T1- or T2-weighted volumes require image intensity correction (Ahsan R L, Allom R, Gousias I S, Habib H, Turkheimer F E, Free S, Lemieux L, Myers R, Duncan J S, Brooks, D J, Koepp M J, Hammers A (2007): Volumes, spatial extents and a probabilistic atlas of the human basal ganglia and thalamus. NeuroImage 38:261-270) while multi-modal MRI methods requires coalignment of all data sets before segmentation (Liu T, Young G, Huang L, Chen N K, Wong S T (2006): 76-space analysis of grey matter diffusivity: methods and applications. Neuroimage 31:51-65; Ali A A, Dale A M, Badea A, Johnson G A (2005): Automated segmentation of neuroanatomical structures in multispectral MR microscopy of the mouse brain. NeuroImage 27:425-435; Hasan K M, Halphen C, Boska M D, Narayana P A (2008a): Diffusion tensor metrics, T2 relaxation, and volumetry of the naturally aging human caudate nuclei in healthy young and middle-aged adults: possible implications for the neurobiology of human brain aging and disease. Magn Reson Med 59:7-13; Pham D L, Xu C, Prince J L (2000): Current methods in medical image segmentation. Annu. Rev. Biomed. Eng. 2:315-337).

To obtain intrinsic tissue relaxation or DTI metrics from certain manually or automatically segmented regions, the acquisition of separate data sets is needed along with perfect multimodal data coregistration and fusion with the T1-weighted volume (Mabbott D J, Noseworthy M, Bouffet E, Laughlin S, Rockel C (2006): White matter growth as a mechanism of cognitive development in children. NeuroImage 33:936-946; Thottakara P, Lazar M, Johnson S C, Alexander A L (2006): Application of Brodmann's area templates for ROI selection in white matter tractography studies. NeuroImage 29:868-878).

The DTI-based tissue contrast method was used to obtain whole brain cerebrospinal fluid (CSF), GM, and white matter (WM) volumes from typically developing children (Hasan K M, Halphen C, Sankar A, Eluvathingal T J, Kramer L, Stuebing K K, Fletcher J M, Ewing-Cobbs L (2007a): Diffusion tensor imaging-based tissue segmentation: validation and application to the developing child and adolescent brain. NeuroImage 34:1497-1505). This DTI-based method was applied to obtain well-documented developing and aging trends of whole brain CSF, GM and WM across the human lifespan (Hasan K M, Sankar A, Halphen C, Kramer L A, Brandt M E, Juranek J, Cirino, P T, Fletcher J M, Papanicolaou A C, Ewing-Cobbs L (2007b): Development and organization of the human brain tissue compartments across the lifespan using diffusion tensor imaging. Neuroreport 18:1735-1739). These DTI-based segmentation methods were validated and extended further to the semi-automated segmentation of WM regions such as the corpus callosum (Hasan K M, Ewing-Cobbs L, Kramer L A, Fletcher J M, Narayana P A (2008b): Diffusion tensor quantification of the macrostructure and microstructure of human midsagittal corpus callosum across the lifespan. NMR Biomed 21:1094-1101; Hasan K M, Kamali A, Kramer L A, Papanicolaou A C, Fletcher J M, Ewing-Cobbs L (2008c): Diffusion tensor quantification of the human midsagittal corpus callosum subdivisions across the lifespan. Brain Research 1227:52-67).

MRI

Magnetic resonance imaging (MRI) is based on imaging water rich soft central nervous tissue. The MRI data acquisition involves water spin polarization or alignment in a strong magnetic field and then the application of timed and controlled spatially dependent magnetic pulses for spatial encoding (FIG. 1). The signal is collected using a radio-frequency tuned near-field coil and then amplified, decoded and visualized to show the water density maps. The MRI contrast can be used to differentiate different tissue types (e.g. gray matter, myelinated white matter and cerebrospinal fluid or abnormal tissue (e.g. demyelination, tumors, and infarcts).

DTI or DTMRI

Diffusion tensor imaging (DTI) or diffusion tensor magnetic resonance imaging (DTMRI) uses the same MRI data acquisition and processing (Basser and Jones 2002). In addition to the standard MRI acquisition paradigm, strong diffusion magnetic pulses (Gx, Gy, Gz) or ($g_x$, $g_y$, $g_z$) are applied along the three gradient channels to obtain diffusion-weighted or contrasted data (FIG. 2).

DTI Contrast

The main principle of diffusion contrast is that water molecular random translational motion will be hindered when water molecules encounter obstacles such as myelinated or compacted tissue. The application of a set of encoding directions with a number greater than six will enable the encoding of the three principal orientations to obtain the diffusion tensor (Basser et al. 1997). The diffusion tensor provides both scalar metrics such as anisotropy and diffusivity in addition to tissue local orientation to quantify and map the microstructural integrity and/or connectivity in the living tissue (FIG. 3).

Diffusion Tensor Analysis Pipeline

The raw or encoded diffusion-weighted data collected undergoes several preprocessing steps before display. These steps include image distortion correction that results from eddy currents upon using large magnetic pulses and then tensor decoding and diagonalization to obtain the eigenvalues and eigenvectors. Conventionally, the eigenvalues are used to compute fractional anisotropy and mean diffusivity (FIG. 4).

The ability to segment whole brain cerebrospinal fluid (CSF) and gray and white matter tissue to provide regional volume and DTI metrics of white matter tract and cortical and subcortical gray matter is important in many clinical applications. Such high resolution brain imaging is needed for accurate detection of congenital defects, diagnosis and determining prognosis of many neurologic disorders, such as, but not limited to brain tumors, traumatic brain injury, Alzheimer's disease, Parkinson's disease, Huntington's disease, swelling of the brain, such as, but not limited to that due to infectious diseases such as meningitis, viral or parasitic diseases. Therefore, there is continuing interest to develop methods and systems in DTI to provide such information.

SUMMARY

Methods and systems for displaying macrostructural volumetry and microstructural integrity and/or connectivity of region of interest (ROI) in a patient are disclosed. Methods and systems for tissue segmentation and atlas-based tissue segmentation in ROI of a patient using diffusion MRI data are also described.

In an embodiment, a method for studying microstructural integrity or connectivity or both of region of interest (ROI) in a patient comprises acquiring, via an imaging system, diffusion magnetic resonance (MRI) data in the ROI by using Icosahedral Diffusion Tensor Encoding Scheme (IDTES); computing, via the imaging system, mean diffusivity (MD) and fractional anisotropy (FA) by using logarithm-moment algorithm (LMA); and displaying, on a display, the microstructural integrity or connectivity or both of ROI based on the computed MD and FA. The diffusion MRI data comprise diffusion-weighted imaging (DWI) data or diffusion tensor imaging (DTI) data. In some cases, displaying the microstructural integrity or connectivity or both of ROI takes place in real time. In various embodiments, the method further comprises generating a training set of the ROI to obtain MD and FA thresholds; and segmenting tissue in the ROI based on the computed MD and FA and the thresholds. In some embodiments, such a method further comprises obtaining an atlas comprising the ROI; and registering the segmented tissue with the atlas. In some cases, registering the segmented tissue with the atlas takes place in real time.

In an embodiment, an imaging system configured for studying microstructural integrity or connectivity or both of region of interest (ROI) in a patient, contains software that, when executed by a processor, causes the processor to acquire diffusion magnetic resonance (MRI) data in the ROI by using Icosahedral Diffusion Tensor Encoding Scheme (IDTES); compute mean diffusivity (MD) and fractional anisotropy (FA) by using logarithm-moment algorithm (LMA); and display the microstructural integrity or connectivity or both of ROI based on the computed MD and FA. In some cases, the display of the microstructural integrity or connectivity or both of ROI based on the computed MD and FA takes place in real time. In some embodiments, the software of the imaging system further causes the processor to generate a training set to obtain MD and FA thresholds; and segment tissue in the ROI based on the computed MD and FA and the thresholds. In further embodiments, the software of the imaging system further causes the processor to obtain an atlas comprising the ROI; and register the segmented tissue with the atlas.

In another embodiment, a method for segmenting tissue in region of interest (ROI) in a patient comprises obtaining, via a computer system, diffusion magnetic resonance (MRI) data in the ROI; computing, via the computer system, mean diffusivity (MD) and fractional anisotropy (FA) from the diffusion MRI data; generating, via the computer system, a training set of the ROI to obtain MD and FA thresholds; and segmenting, via the computer system, tissue in the ROI based on the computed MD and FA and the thresholds. The diffusion MRI data comprise diffusion-weighted imaging (DWI) data or diffusion tensor imaging (DTI) data. Tissue in the ROI comprises gray matter (GM), white matter (WM), or cerebrospinal fluid (CSF). In some embodiments, this method further comprises obtaining an atlas comprising the ROI; and registering the segmented tissue with the atlas. In some cases, this method takes place in real time while the diffusion MRI data are being obtained. In some other cases, this method takes place after the diffusion MRI data have been obtained.

In yet another embodiment, a computer-readable storage medium (CRSM) contains software that, when executed by a processor, causes the processor to obtain diffusion magnetic resonance (MRI) data in region of interest (ROI) in a patient; compute mean diffusivity (MD) and fractional anisotropy (FA) from the diffusion MRI data; generate a training set of the ROI to obtain MD and FA thresholds; and segment tissue in the ROI based on the computed MD and FA and the thresholds. In some cases, the software further causes the processor to obtain an atlas comprising the ROI; and register the segmented tissue with the atlas.

In a further embodiment, a method comprises acquiring, via an imaging system, diffusion magnetic resonance (MRI) data in region of interest (ROI) in a patient by using Icosahedral Diffusion Tensor Encoding Scheme (IDTES); computing, via the imaging system, mean diffusivity (MD) and fractional anisotropy (FA) by using logarithm-moment algorithm (LMA); generating, via the imaging system, a training set of the ROI to obtain MD and FA thresholds; segmenting, via the imaging system, tissue in the ROI based on the computed MD and FA and the thresholds; obtaining, via the imaging system, an atlas comprising the ROI; and registering, via the imaging system, the segmented tissue with the atlas. In some embodiments, such a method takes place in real time and is executable by a software contained in a computer-readable storage medium (CRSM).

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION

Definitions

Figure 1:
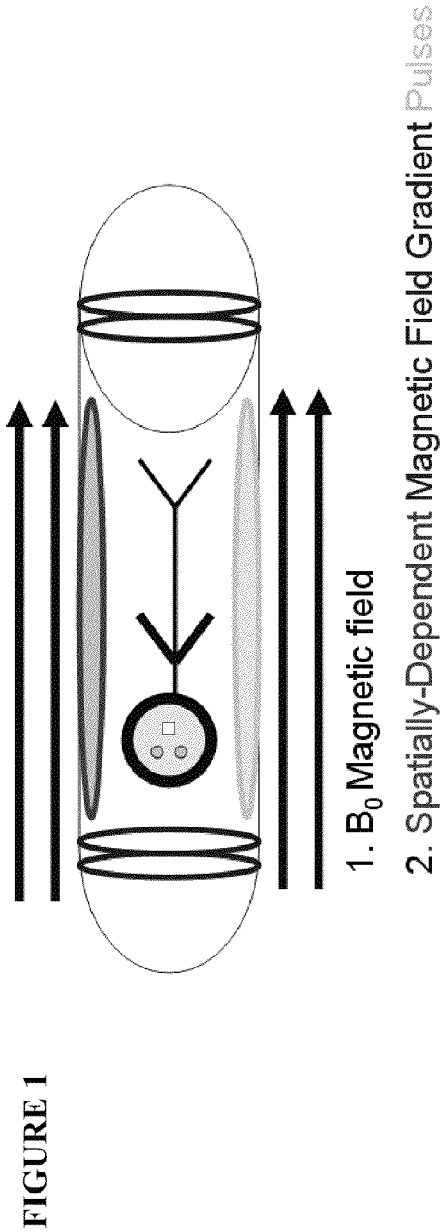
FIG. 1 is a schematic illustration of a patient in magnetic fields for an MRI scan, wherein said magnetic fields comprise a static magnetic field $B_0$ and spatially dependent magnetic field gradients/pulses for spatial encoding.
Figure 3:
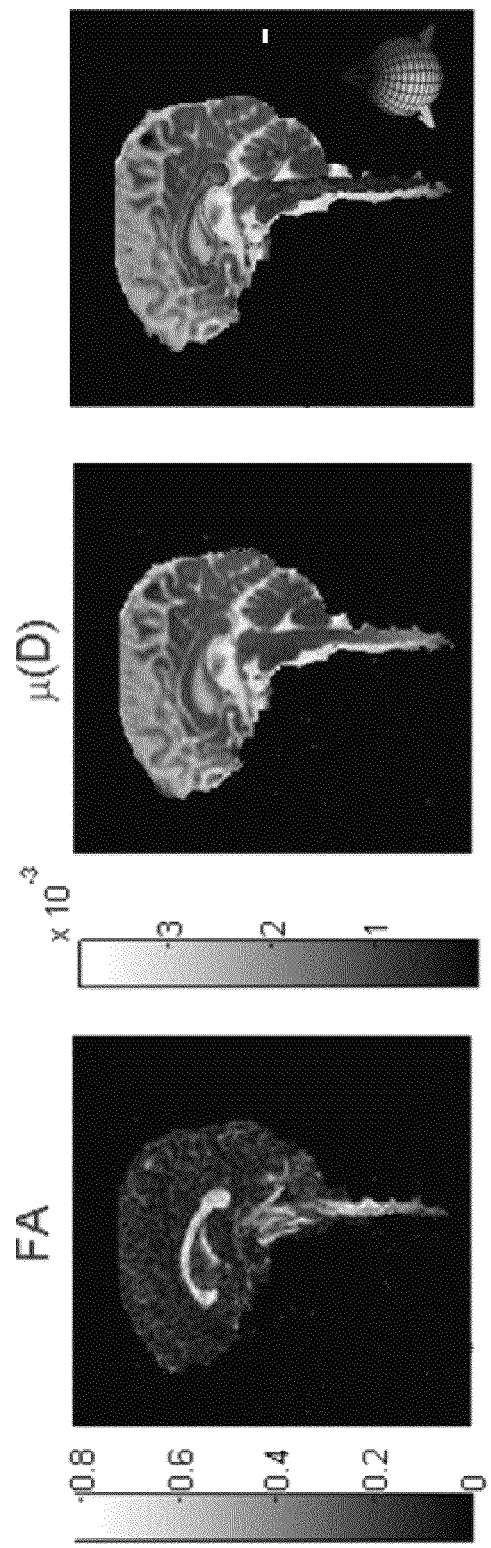
FIG. 3 illustrates the diffusion tensor that provides both scalar metrics such as anisotropy and diffusivity in addition to tissue local orientation to quantify and map the microstructural integrity and/or connectivity in the tissue.
Figure 2:
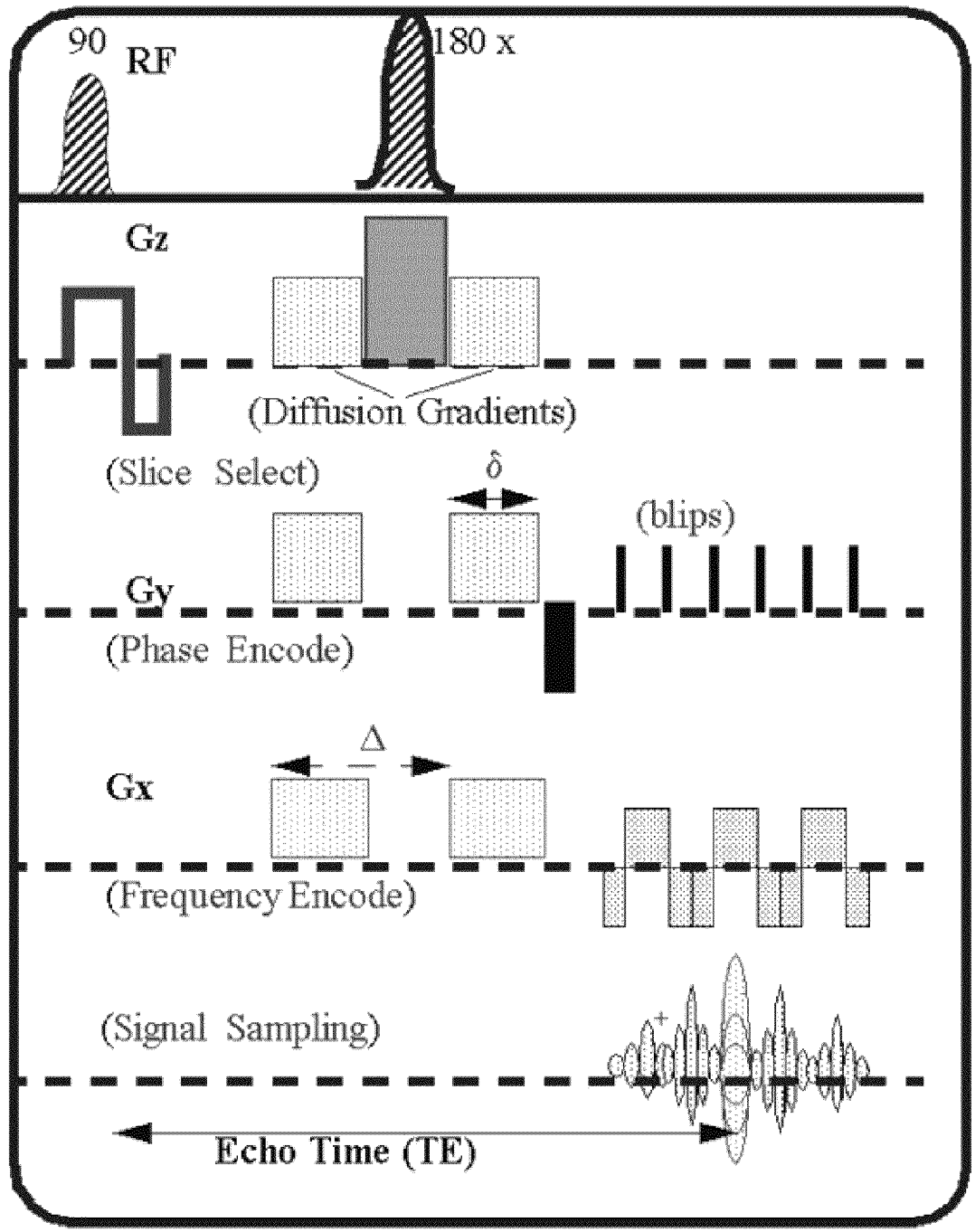
FIG. 2 illustrates diffusion magnetic pulses (Gx, Gy, Gz) or ($g_x$, $g_y$, $g_z$) applied along the three gradient channels to obtain diffusion-weighted or contrasted data in diffusion tensor imaging (DTI).
Figure 4:
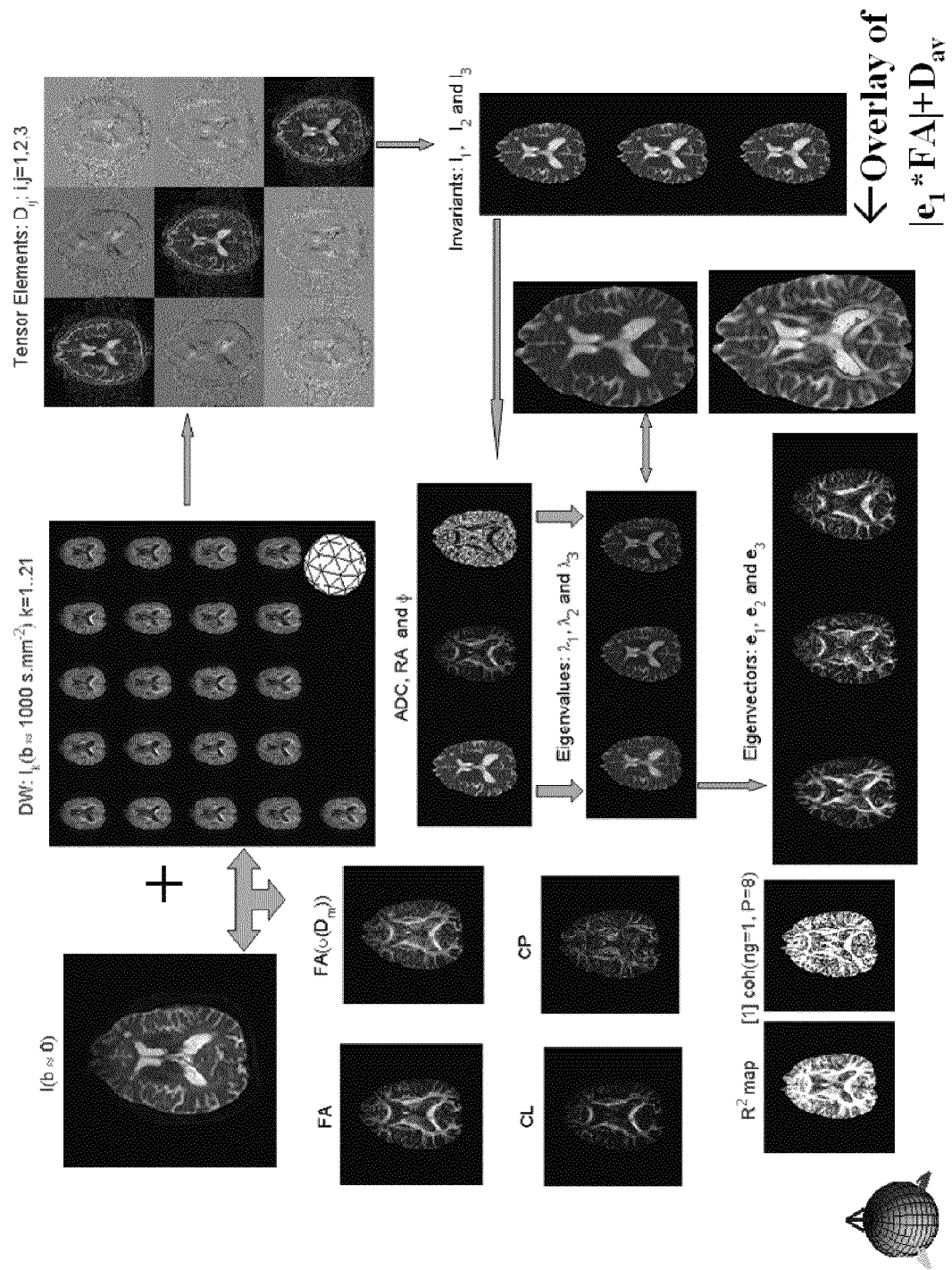
FIG. 4 illustrates the preprocessing steps of collected raw or encoded diffusion-weighted MRI data before display. These steps may include image distortion correction that results from eddy currents upon using large magnetic pulses; tensor decoding and diagonalization to obtain the eigenvalues and eigenvectors. The eigenvalues are used to compute fractional anisotropy (FA) and mean diffusivity (MD).

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, and unless otherwise indicated, the terms "treat", "treating", and "treatment" contemplate an action that occurs while a patient is suffering from neurologic disorders that reduces the severity of one or more symptoms or effects of neurologic or a related disease or disorder. Where the context allows, the terms "treat", "treating", and "treatment" also refers to actions taken toward ensuring that individuals at increased risk of neurologic disorders are able to receive appropriate neurosurgical or other medical intervention prior to onset of neurologic disorders. As used herein, and unless otherwise indicated, the terms "prevent", "preventing", and "prevention" contemplate an action that occurs before a patient begins to suffer from neurologic disorders, that delays the onset of, and/or inhibits or reduces the severity of, neurologic disorders. As used herein, and unless otherwise indicated, the terms "manage", "managing", and "management" encompass preventing, delaying, or reducing the severity of a recurrence of neurologic disorders in a patient who has already suffered from such a disease or condition. The terms encompass modulating the threshold, development, and/or duration of the neurologic disorders or changing how a patient responds to the neurologic disorders.

High resolution brain imaging, such as that described in the present disclosure can be used as a quantitative surrogate marker for therapies in clinical trials and is critical for accurate detection of congenital defects (such as spina bifida), diagnosis and determining the prognosis of many neurologic disorders, such as, but not limited to neurologic disorders which include, but are not limited to, those associated with natural brain development and aging, senile dementia, learning disabilities (dyslexia, math), schizophrenia, depression, bipolar disorders, autism, epilepsy, amyotrophic lateral sclerosis (ALS), Alzheimer's disease, Parkinson's disease, Huntington's disease, traumatic brain injury, stroke, multiple sclerosis, brain tumors (for example, glioblastoma (GBM), astrocytoma), swelling or damage to the brain, such as, but not limited to that resulting from infectious diseases such as meningitis, viral or parasitic diseases, HIV as well as brain injury due to exposure to neurotoxins (cocaine-addiction, chronic alcoholism).

In this disclosure, the term "real-time" or "real time" refers to activities that take place within one session of an MRI scan for a patient. For example, "real-time" display of the brain structures refers to the ability to display the brain structures while the patient is being scanned in an MRI session.

In this disclosure, a computer-readable storage medium (CRSM) comprises volatile storage (e.g., random access memory), non-volatile storage (e.g., hard disk drive, compact disc, flash storage, read only memory, etc.), or combinations thereof.

Overview

In various embodiments, a method for real-time display of brain structures is described. Such a method utilizes an Icosahedral Diffusion Tensor Encoding Scheme (IDTES) to obtain DTI data (or DWI data) and computes the mean diffusivity (MD) and fractional anisotropy (FA) using the icosahedral properties. A system that is capable of performing such a method is also disclosed.

In other embodiments, a method for regional segmentation of brain tissue is described. This method comprises obtaining DTI data (or DWI data) and computing the mean diffusivity (MD) and fractional anisotropy (FA) of brain structures. It further comprises segmenting brain tissue based on the computed MD and FA; registering the segmented tissue with an atlas; and performing atlas-based brain tissue segmentation. A system that is capable of carrying out this method is also disclosed.

In yet other embodiments, a method for real-time regional segmentation of brain tissue is described. This method utilizes an Icosahedral Diffusion Tensor Encoding Scheme (IDTES) to obtain DTI data (or DWI data) and computes the mean diffusivity (MD) and fractional anisotropy (FA) using the icosahedral properties. This method further comprises segmenting brain tissue based on the computed MD and FA; registering the segmented tissue with an atlas; and performing atlas-based brain tissue segmentation in real time. A system that is capable of carrying out this method is also disclosed.

Icosahedral Diffusion Tensor Encoding Scheme (IDTES)

Figure 8:
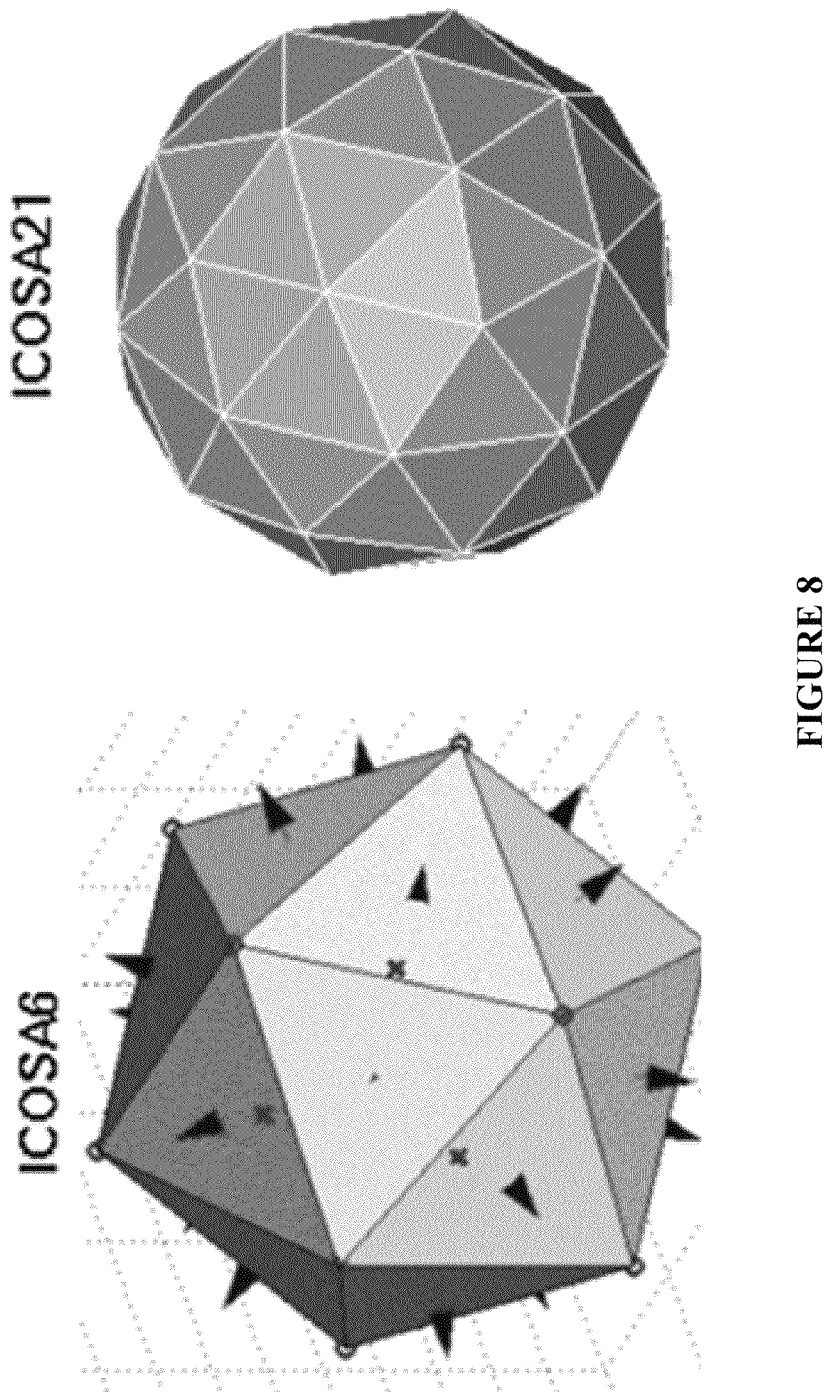
FIG. 8 shows the space vertices defined by ICOSA6 and ICOSA 21.

An Icosahedral Diffusion Tensor Encoding Scheme (IDTES) utilizes a scheme as shown in Table 1, Table 2, or Table 3 to encode the magnetic pulses (Gx, Gy, Gz) or ($g_x$, $g_y$, $g_z$) applied along the three gradient channels to obtain diffusion-weighted or contrasted DTI data. Table 1 shows "ICOSA6" as an IDTES; Table 2 shows "ICOSA15" as a different IDTES; and Table 3 shows "ICOSA21" as yet another IDTES. FIG. 8 shows the space vertices defined by "ICOSA6" and "ICOSA21".

TABLE 1

| | # | | | | | |
|---|---|---|---|---|---|---|
| $g_i$ | 4 | 5 | 6 | 7 | 8 | 9 |
| $g_x$ | 0 | 0 | A | A | −B | −B |
| $g_y$ | A | −A | −B | B | 0 | 0 |
| $g_z$ | −B | −B | 0 | 0 | A | −A | wherein
$\tau = 2\cos(\pi/5)$;
$A = 1/\sqrt{(1+\tau^2)}$;
$B = \tau/\sqrt{(1+\tau^2)}$;
$C = (\tau-1)/2$;
$D = \tau/2$

TABLE 2

| | # | | | | | | | | | | | | | | |
|---|---|---|---|---|---|---|---|---|---|---|---|---|---|---|---|
| $g_i$ | 1 | 2 | 3 | 10 | 11 | 12 | 13 | 14 | 15 | 16 | 17 | 18 | 19 | 20 | 21 |
| $g_x$ | 1.0 | 0.0 | 0.0 | C | C | −C | C | −0.5 | 0.5 | 0.5 | 0.5 | −D | D | D | −D |
| $g_y$ | 0.0 | 1.0 | 0.0 | −D | D | −D | −D | C | −C | C | C | 0.5 | −0.5 | 0.5 | −0.5 |
| $g_z$ | 0.0 | 0.0 | 1.0 | −0.5 | −0.5 | −0.5 | 0.5 | D | D | −D | D | C | C | −C | −C | wherein
$\tau = 2\cos(\pi/5)$;
$A = 1/\sqrt{(1+\tau^2)}$;
$B = \tau/\sqrt{(1+\tau^2)}$;
$C = (\tau-1)/2$;
$D = \tau/2$

TABLE 3

| | # | | | | | | | | | | |
|---|---|---|---|---|---|---|---|---|---|---|---|
| $g_i$ | 1 | 2 | 3 | 4 | 5 | 6 | 7 | 8 | 9 | 10 | 11 |
| $g_x$ | 1.0 | 0.0 | 0.0 | 0 | 0 | A | A | −B | −B | C | C |
| $g_y$ | 0.0 | 1.0 | 0.0 | A | −A | −B | B | 0 | 0 | −D | D |
| $g_z$ | 0.0 | 0.0 | 1.0 | −B | −B | 0 | 0 | A | −A | −0.5 | −0.5 |

| | # | | | | | | | | | |
|---|---|---|---|---|---|---|---|---|---|---|
| $g_i$ | 12 | 13 | 14 | 15 | 16 | 17 | 18 | 19 | 20 | 21 |
| $g_x$ | −C | C | −0.5 | 0.5 | 0.5 | 0.5 | −D | D | D | −D |
| $g_y$ | −D | −D | C | −C | C | C | 0.5 | −0.5 | 0.5 | −0.5 |
| $g_z$ | −0.5 | 0.5 | D | D | −D | D | C | C | −C | −C | wherein
$\tau = 2\cos(\pi/5)$;
$A = 1/\sqrt{(1+\tau^2)}$;
$B = \tau/\sqrt{(1+\tau^2)}$;
$C = (\tau-1)/2$;
$D = \tau/2$ The orthogonal xyz directions (S3) are #[1, 2, 3]. The condition number of ICOSA6, ICOSA15 and ICOSA21 is $\sqrt{10}/2 \sim 1.581$

S9=ICOSA6+S3; S12=ICOSA15−S3; S18=ICOSA21−S3

Note that the 7 sets: S3, S9, S12, S18, ICOSA6, ICOSA15, AND ICOSA21 satisfy the requirement that $\text{Sum}_c(H)*d/N_e = D_{av}$. Average diffusivity ($D_{av}$) is computed directly using the diffusion-weighted data using Icosa21b_ord in 7 different ways at constant $SNR_0$. $N_e=6$ for ICOSA6, 15 for ICOSA15, and 21 for ICOSA21.

$$\alpha_{min} \cong \frac{180}{\pi}\arctan(2.0)\sqrt{\frac{5}{N_e-1}} = 63.4349^0 \sqrt{\frac{5}{N_e-1}}$$

The sequence for applying the magnetic pulses (Gx, Gy, Gz) or ($g_x$, $g_y$, $g_z$) along the three gradient channels may be any within each IDTES. For example, the IDTES of "ICOSA6" as shown in Table 1 may also be applied as shown in Table 4.

TABLE 4

| $g_i$ | # | | | | | |
|---|---|---|---|---|---|---|
| | 7 | 4 | 5 | 9 | 6 | 8 |
| $g_x$ | A | 0 | 0 | −B | A | −B |
| $g_y$ | B | A | −A | 0 | −B | 0 |
| $g_z$ | 0 | −B | −B | −A | 0 | A | wherein
$\tau = 2\cos(\pi/5)$;
$A = 1/\sqrt{(1+\tau^2)}$;
$B = \tau/\sqrt{(1+\tau^2)}$;
$C = (\tau-1)/2$;
$D = \tau/2$ The signal intensity of a reference or non-diffusion weighted data point ($I_0$) is also acquired, wherein $I_0(x, y, z)$ corresponds to $g_x=0$, $g_y=0$, and $g_z=0$. In some cases, multiple IDTESs may be used to obtain DTI/DWI data and for each IDTES, the signal-to-noise ratio (SNR) is estimated.

Computation of FA and MD

After diffusion-weighted data or DTI data are acquired using the IDTES, fractional anisotropy (FA) and mean diffusivity (MD) are computed from the intensity of the DTI data or diffusion-weighted data by a logarithm-moment algorithm (LMA) as shown below.

Figure 9:
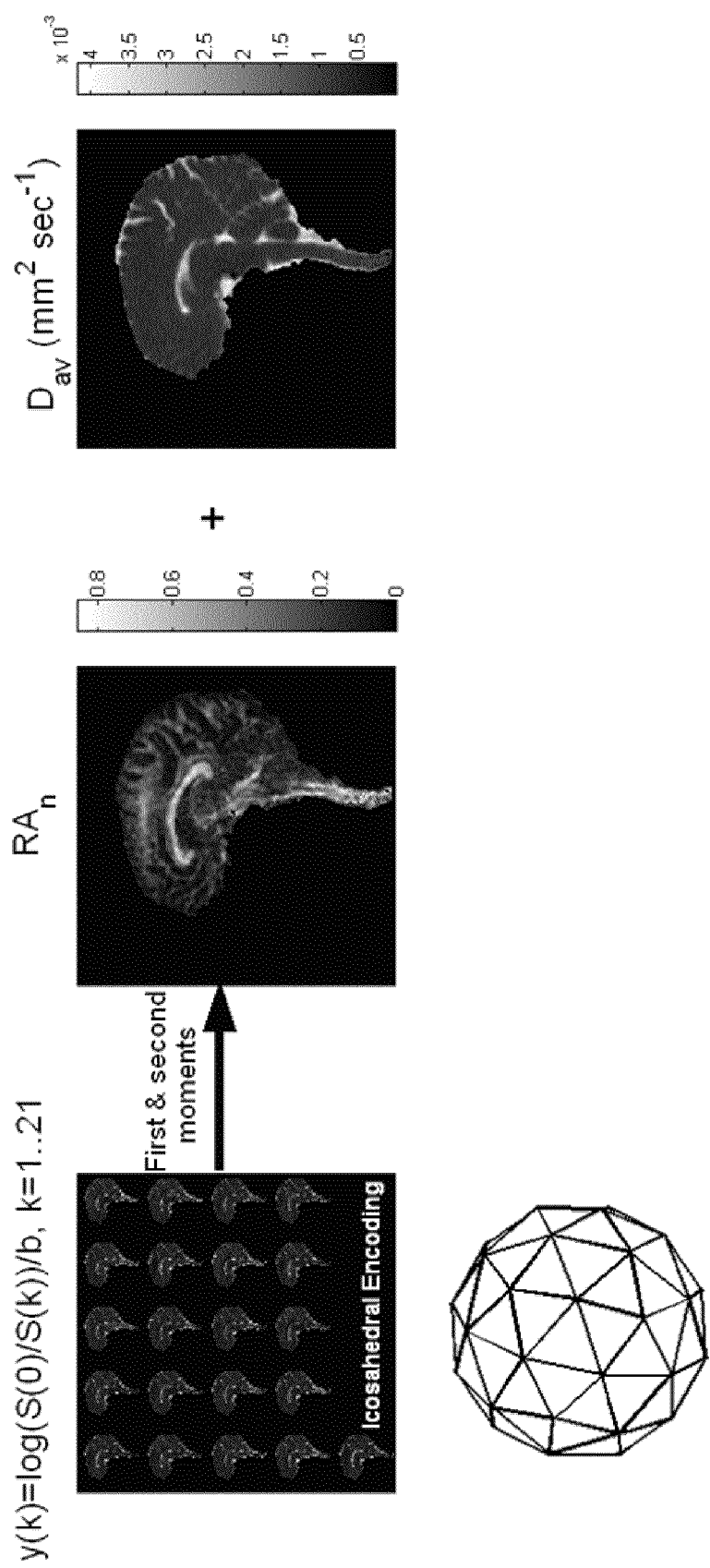
FIG. 9 illustrates the computation of relative anisotropy (RA) and average diffusivity ($D_{av}$) from raw diffusion MRI data acquired using ICOSA21.

For each voxel x, y, z; initialize S= and S2=0
For k=1 to Ne $ADC_k(x,y,z) = [\log(I_0(x,y,z)) - \log(I_k(x,y,z))]/b$ $S = S + ADC_k$ $S2 = S2 + (ADC_k)^2$ End The signal intensity I of the diffusion-weighted data is logarithm-transformed and subtracted from the logarithm-transformed reference scan $I_0$ to compute the Apparent Diffusion Coefficient (ADC) for the $k^{th}$ encoding direction using b as the diffusion sensitization factor. This quantity is computed, incremented, and summed in real time for the Ne encoding directions to obtain the sum S and the sum of squares S2. The mean diffusivity (MD) is then computed as the accumulated sum S/Ne and the fractional anisotropy (FA) is computed from the relative anisotropy (RA). The first moment of the DTI signal intensity is the mean; the second moment is the standard deviation. FIG. 9 illustrates the computation of RA and $D_{av}$ from raw diffusion MRI data acquired using ICOSA21.

$MD = S/Ne$;

$RA = \text{sqrt}([S2 - S*S/Ne]/(Ne-1))$;

$FA = \text{sqrt}([3/(1/(RA*RA)+2)])$.

When DTI data are acquired using the IDTES and the FA and MD are computed using LMA, real-time display or mapping of the micro-structural integrity and/or connectivity in the living tissue is realized.

Generation of Training Set for DTI Tissue Segmentation

Figure 5:
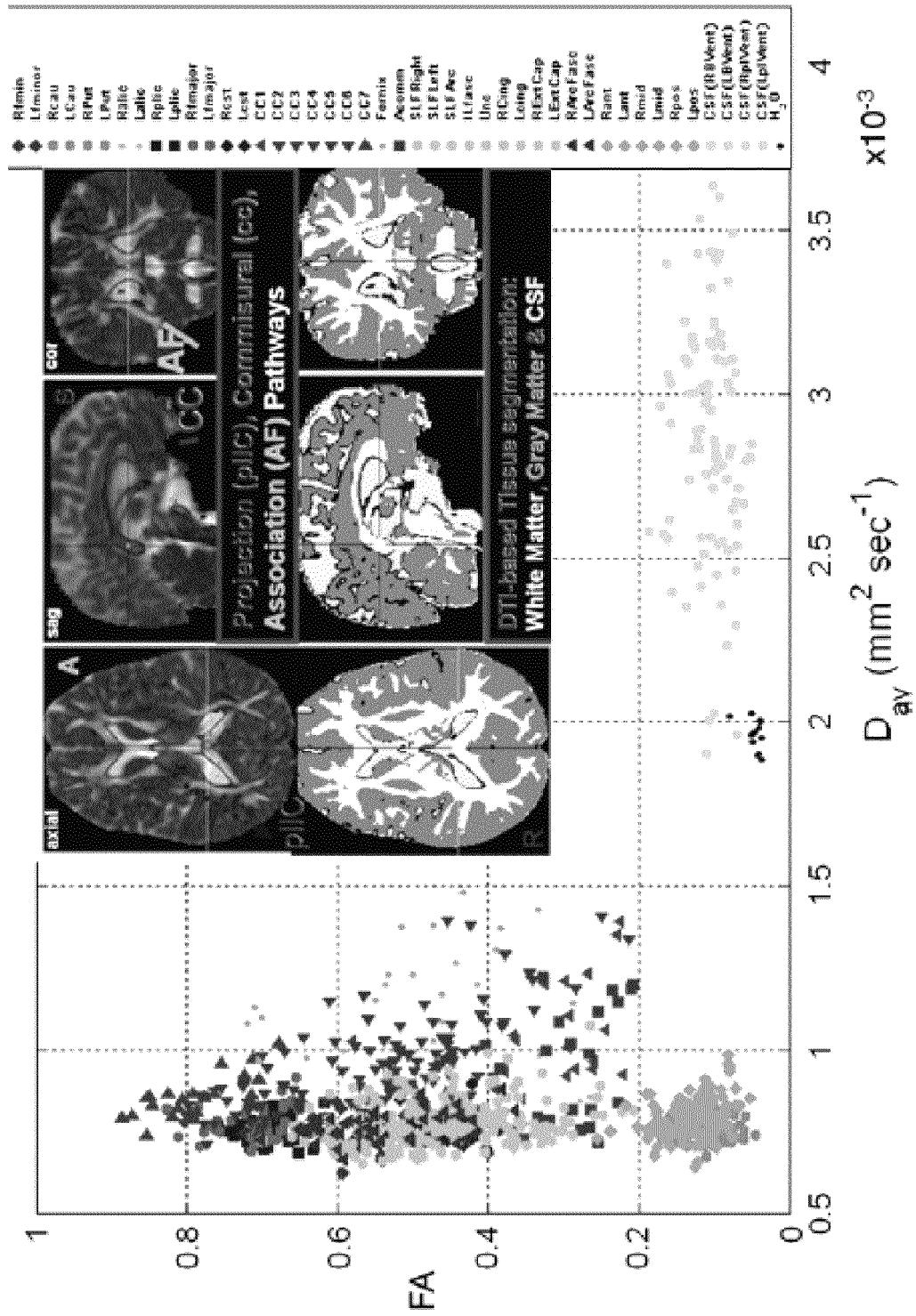
FIG. 5 illustrates tissue segmentation by using a training set based on DTI anisotropy and diffusivity for soft brain tissue.
Figure 6:
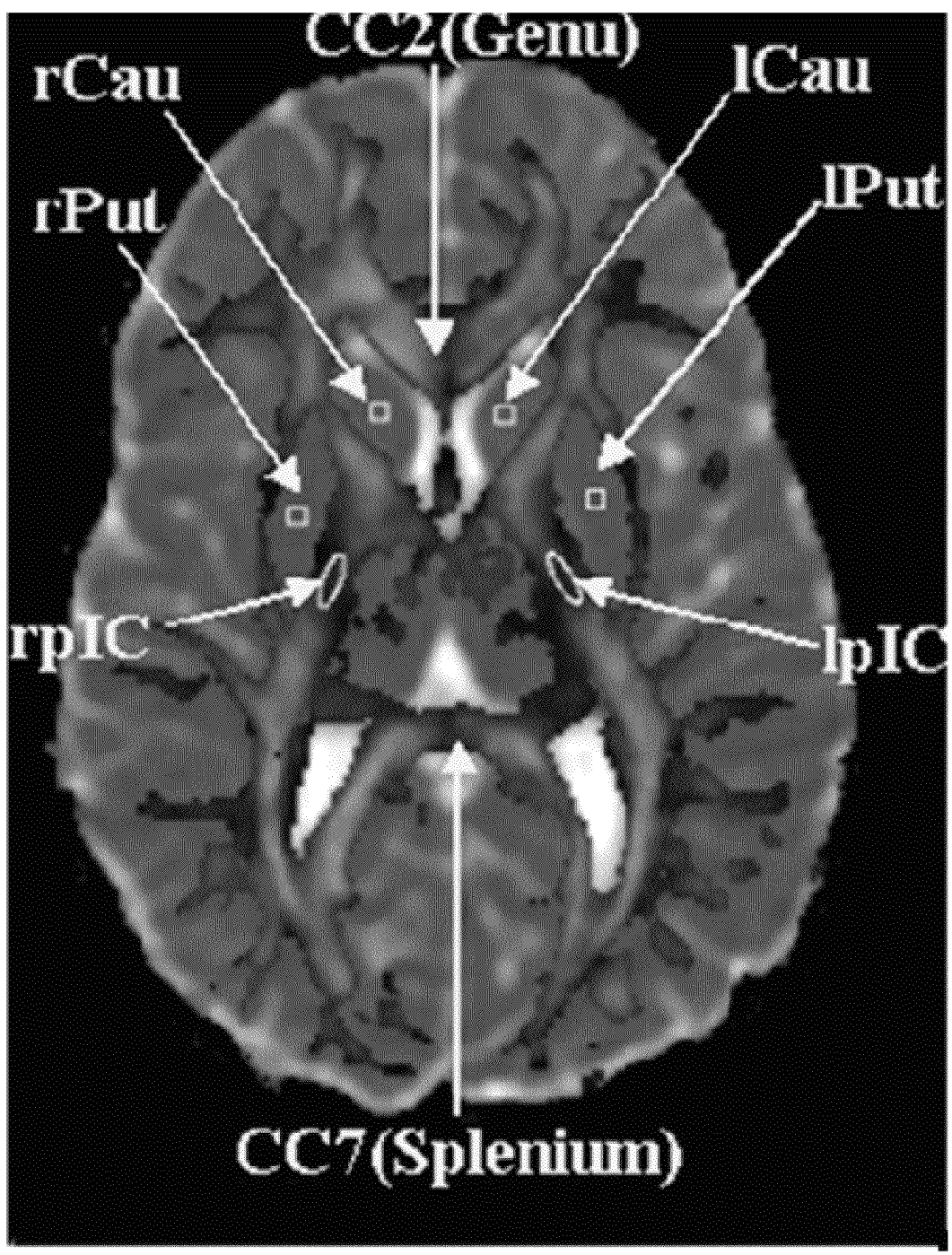
FIG. 6 illustrates the generation of a training set by computing FA and MD values in regions-of-interest from a population of controls or patients using labeled anatomical landmarks.
Figure 7:
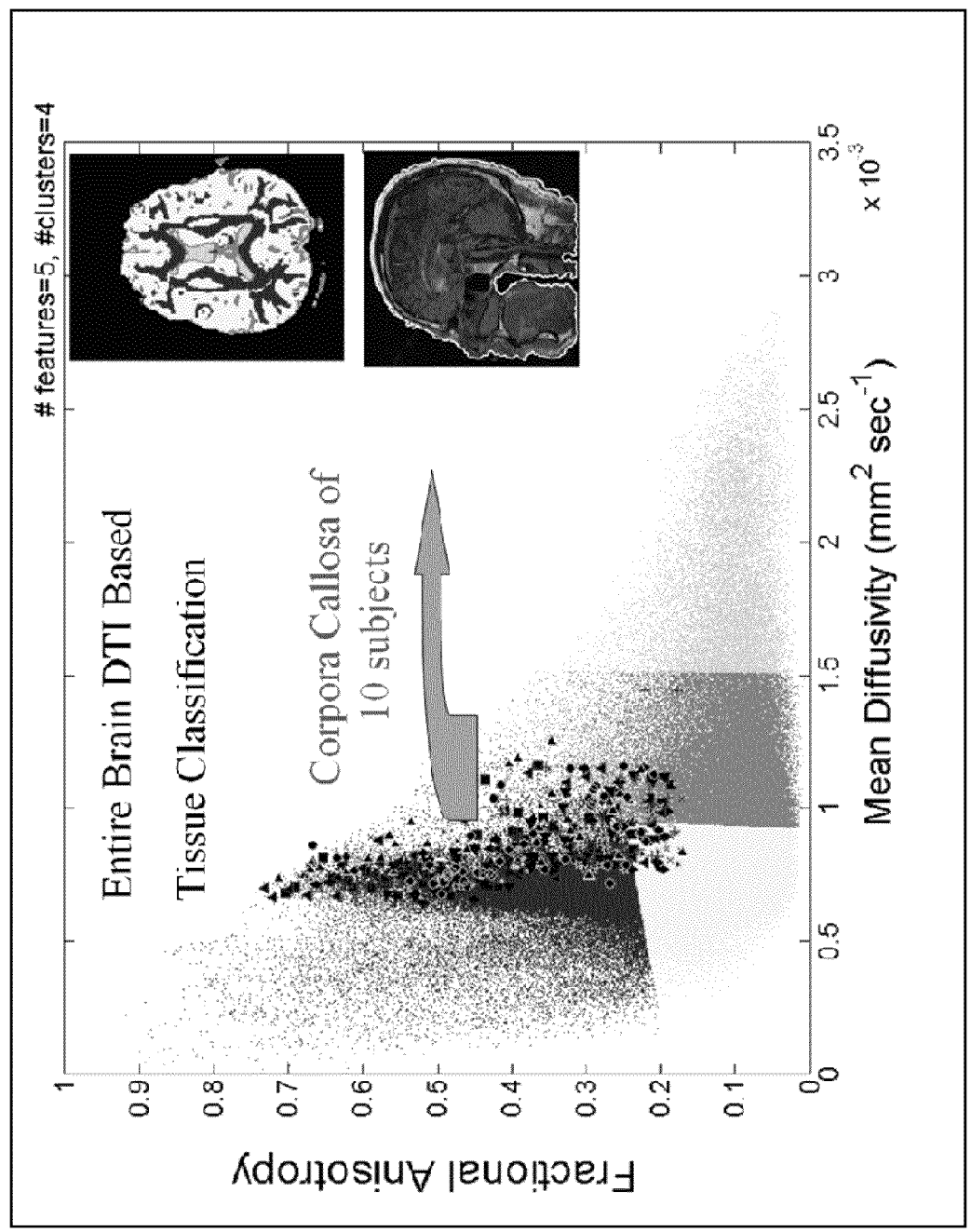
FIG. 7 illustrates tissue segmentation applied globally and regionally to corpus callosum.

A training set is generated from a population of controls or patients using labeled anatomical landmarks (FIG. 6). The FA and MD of regions of interest (ROI) are computed by any conventional method or the method disclosed herein after DTI data is acquired. The FA and MD values obtained are tested for reproducibility using same rater and multiple raters. These values are then analyzed to obtain the mean and standard deviation for each subgroup as function of side (right vs. left), age and gender (males vs. females). The optimal values obtained (FIG. 5) provide statistical thresholds for FA and MD that enable tissue segmentation. Such a method may also be applied globally and regionally to structures such as the corpus callosum (FIG. 7). An atlas may be used to register the segmented tissue. This process may be applied in real time or retrospectively after DTI/DWI data have been acquired.

Real Time and Atlas-based DTI Tissue Segmentation

In various embodiments, a method for real-time atlas-based tissue segmentation comprises acquiring DTI data utilizing an IDTES; computing MD and FA values using LMA; and displaying the microstructural integrity and/or connectivity of tissue. This method further comprises generating a training set to obtain MD and FA thresholds; segmenting tissue based on the computed MD and FA values and the MD and FA thresholds; and registering the segmented tissue with an atlas. The atlas may be obtained from an existing braining mapping database (e.g., international consortium for braining mapping, ICBM).

Figure 10:
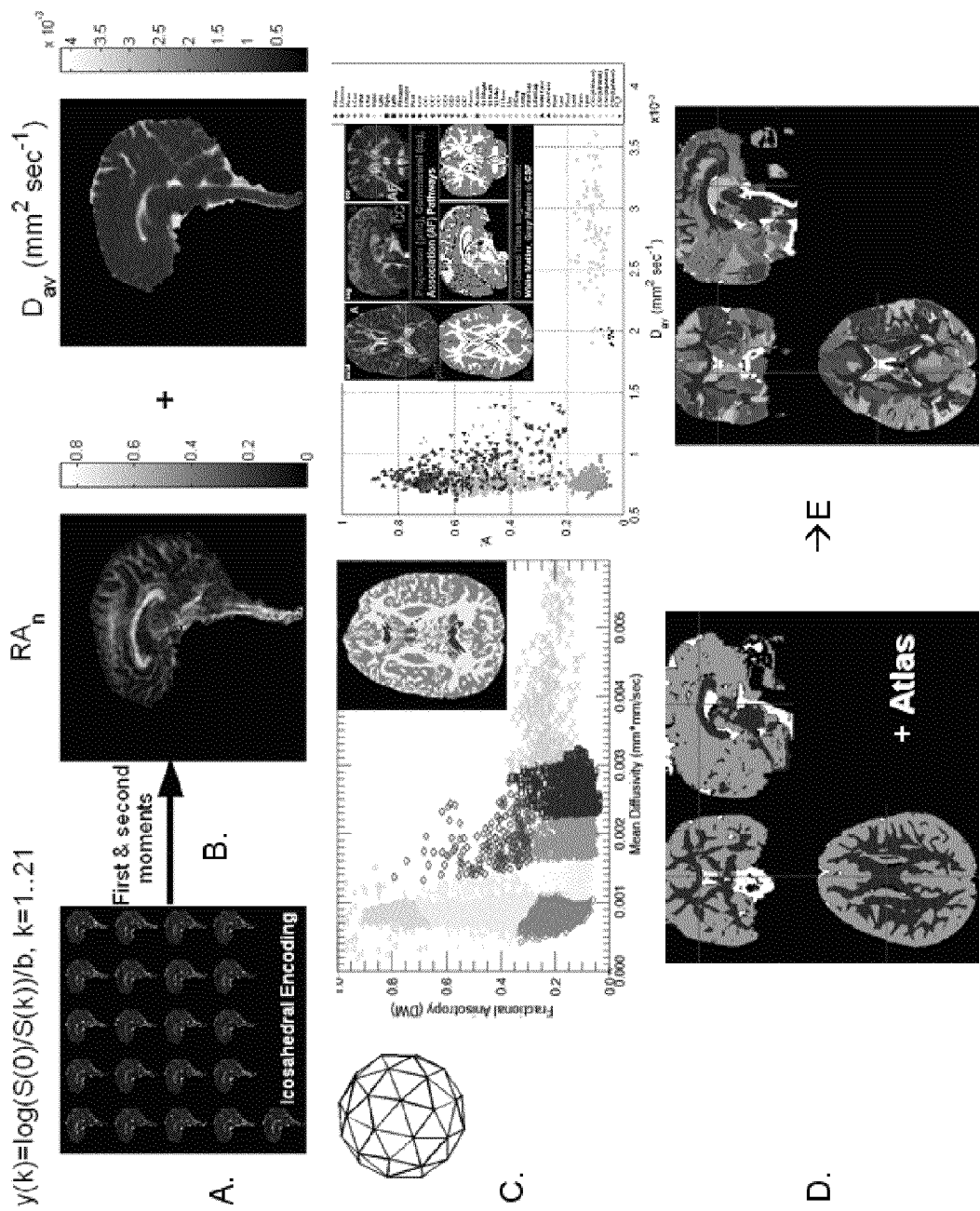
FIG. 10 is an illustration of the multi-faceted encoding scheme characteristics and description of tissue segmentation method using human brain data acquired using echo planar imaging (A) raw data acquired using the ICOSA21, (B) real time estimated RA, $D_{av}$ (which can be used to estimate FA, and eigenvalues, (C) basic tissue segmentation procedures and the building of the feature space and atlas for multiple subjects, (D) building of specific and optimal contrast maps for tissue segmentation, and (E) generation of the labeled volume.
Figure 11:
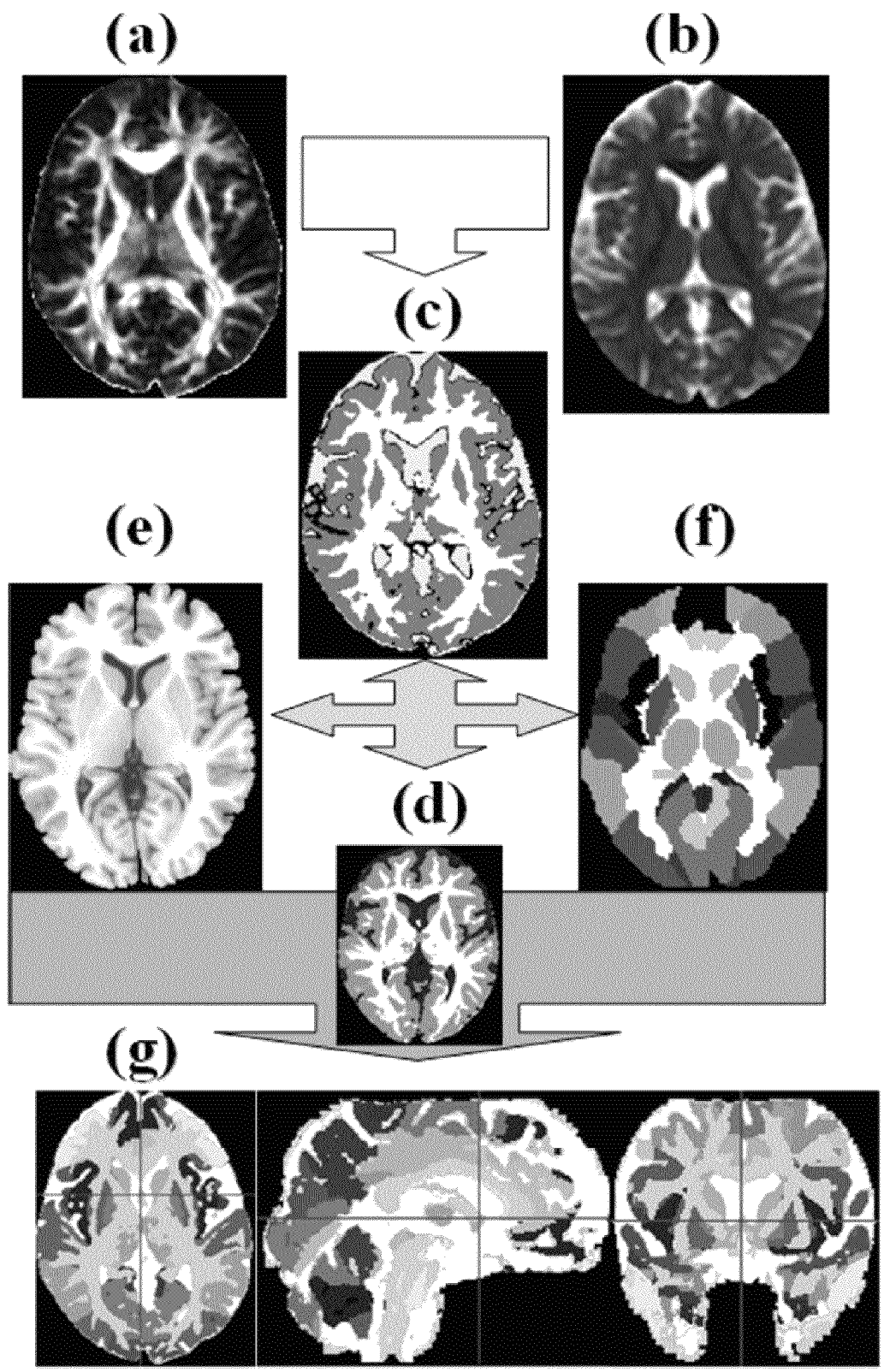
FIG. 11 is a pictorial illustration of the DTI-based atlas-driven method for regional volume estimation: (a) the fractional anisotropy and (b) diffusivity maps are used to (c) cluster brain tissues into GM, white matter and CSF. The tissue map is normalized (d) using the ICBM/MNI (e) templates and (f) labeled atlases and then transformed back in SPM to each subject's original space (g). The results shown in (g) are viewed in both sagittal and coronal planes. Note that the ICBM atlas used in this illustration contains both lobar cortical regions and subcortical structures. The CSF is assigned a yellow color in (c) and white color in (g) in colored images.

The atlas-based tissue segmentation (FIG. 10) may be used to provide atlas-based estimation of tissue volumetry and integrity (e.g. anisotropy and diffusivity). Since most atlas-based approaches use a T2w or T1w data set, the contrast in the FA and diffusivity maps may be used to obtain T1w-like contrast to enable the use of packages such as SPM which uses a template along with a labeled atlas such as those provided by the international consortium for brain mapping (FIG. 11).

Systems

Figure 20:
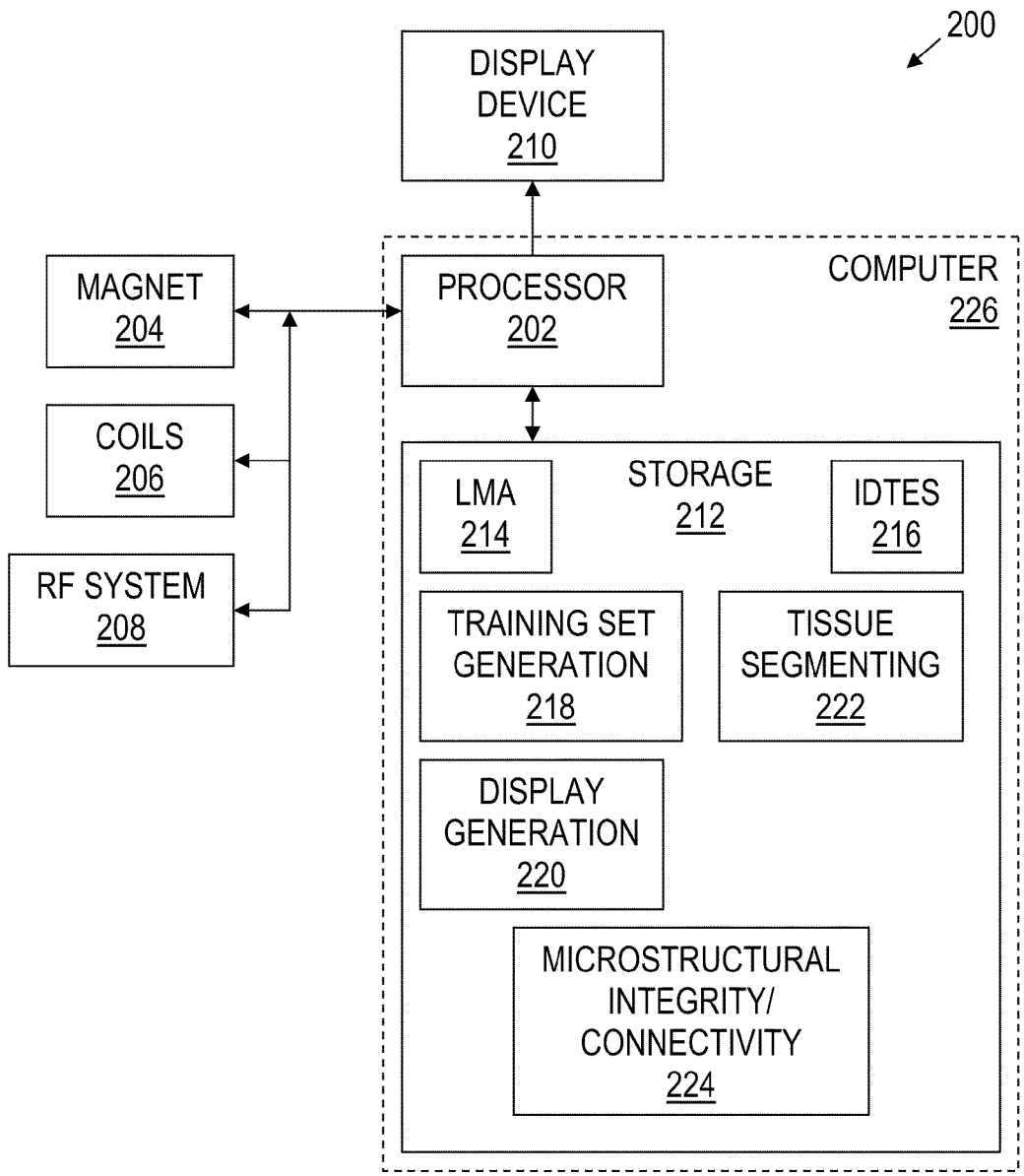
FIG. 20 shows a block diagram of an imaging system in accordance with various embodiments.

FIG. 20 shows a block diagram of a magnetic resonance (MR) imaging system 200 in accordance with various embodiments. The system 200 includes a main magnet 204 to polarize the sample/subject/patient; shim coils 206 for correcting inhomogeneities in the main magnetic field; gradient coils 206 to localize the MR signal; a radio frequency (RF) system 208 which excites the sample/subject/patient and detects the resulting MR signal; and one or more computers 226 to control the aforementioned system components.

A computer 226 of the imaging system 200 comprises a processor 202 and storage 212. Suitable processors include, for example, general-purpose processors, digital signal processors, and microcontrollers. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems. The storage 212 includes a computer-readable storage medium.

Software programming executable by the processor 202 is stored in the storage 212. More specifically, the storage 212 contains software instructions that, when executed by the processor 202, causes the processor 202 to acquire diffusion magnetic resonance (MRI) data in the ROI by using Icosahedral Diffusion Tensor Encoding Scheme (IDTES) (IDTES module 216); compute mean diffusivity (MD) and fractional anisotropy (FA) by using logarithm-moment algorithm (LMA) (LMA module 214); and display (e.g., on display device 210, which may be any device suitable for displaying graphic data) the microstructural integrity and/or connectivity of ROI based on the computed MD and FA (microstructural integrity/connectivity module 224). More particularly, the software instructions stored in the storage 212 cause the processor 202 to display the microstructural integrity and/or connectivity of ROI based on the computed MD and FA in real time (i.e., when the sample/subject/patient is being scanned). Furthermore, the software instructions stored in the storage 212 cause the processor 202 to generate a training set to obtain MD and FA thresholds (training set generation 218); and segment tissue in the ROI based on the computed MD and FA and the thresholds (tissue segmenting 222).

Additionally, the software instructions stored in the storage 212 cause the processor 202 to perform various other operations described herein. For example, the software instructions stored in the storage 212 may cause the processor 202 to obtain an atlas comprising the ROI; and register the segmented tissue with the atlas. In some cases, generating the training set or segmenting tissue or obtaining the atlas or registering the segmented tissue with the atlas takes place on a second computer of the imaging system. (Even if the second computer is not originally or initially part of the imaging system 200, it is considered in the context of this disclosure as part of the imaging system 200.) In this disclosure, the computers 226 of the imaging system 200 are interconnected and are capable of communicating with one another and performing tasks in an integrated manner. For example, each computer is able to access another's storage.

The imaging system 200 is capable of displaying microstructural integrity and/or connectivity of ROI in real time and capable of performing atlas-based tissue segmentation of ROI in real time. For example, the software instructions stored in the storage 212 cause the processor 202 to perform the following actions: acquiring diffusion magnetic resonance (MRI) data in region of interest (ROI) in a patient by using Icosahedral Diffusion Tensor Encoding Scheme (IDTES); computing mean diffusivity (MD) and fractional anisotropy (FA) by using logarithm-moment algorithm (LMA); generating a training set of the ROI to obtain MD and FA thresholds; segmenting tissue in the ROI based on the computed MD and FA and the thresholds; obtaining an atlas comprising the ROI; and registering the segmented tissue with the atlas.

In other cases, a computer system (similar to the computer 226), whether being a part of the imaging system 200 or not, is used for post-processing of diffusion MRI data that have been acquired. In this disclosure, such a computer system comprise one or more computers and the computers are interconnected and are capable of communicating with one another and performing tasks in an integrated manner. For example, each computer is able to access another's storage. Such a computer system comprises a processor and a computer-readable storage medium (CRSM). The CRSM contains software that, when executed by the processor, causes the processor to obtain diffusion magnetic resonance (MRI) data in region of interest (ROI) in a patient; compute mean diffusivity (MD) and fractional anisotropy (FA) from the diffusion MRI data; generate a training set of the ROI to obtain MD and FA thresholds; and segment tissue in the ROI based on the computed MD and FA and the thresholds. The software further causes the processor to obtain an atlas comprising the ROI; and register the segmented tissue with the atlas.

Advantages

Acquisition of DT-MRI (or DWI) data in real time is enabled by using IDTES. It may also provide multiple signal-to-noise (SNR) estimations. This method offers quality control for intrascan reproducibility. Real-time computation of MD and FA is realized using the Icosahedral properties. Such a method may also be implemented retrospectively as a post processing procedure on DTI/DWI data acquired and saved. It enables the obtaining of micro (DTI metrics) and macro (volume) aspects of tissue parameters for diagnosis and assessment of therapy.

EXAMPLES

Example 1

Human Subjects: The participants included 136 right-handed healthy adolescents, young and older adults aged 15.8-62.8 years. The volunteer cohort was pooled from two ongoing studies. The cohort consisted of 65 males (age mean±S.D=31.2±11.5 years), and 71 females (age mean±S.D=34.8±11.7 years). All volunteers were identified as neurologically normal by review of medical history and were medically stable at the time of the assessments. Written informed consent was obtained from the guardians and adolescents and assent from the children participating in these studies per the University of Texas Health Science Center at Houston institutional review board regulations for the protection of human research subjects.

Conventional MRI Data Acquisition: Whole-brain data was acquired using a Philips 3.0 T Intera system with a SENSE parallel imaging receive head coil. The conventional MRI data acquisition protocol included a 2D dual spin-echo TE1/TE2/TR=10/90/5000 ms, in the axial plane (3 mm slice thickness, square field-of-view=240 mm×240 mm @44 sections) and a high spatial resolution spoiled gradient echo sequence acquired using ~180 sagittal sections covering the whole brain with isotropic voxel dimensions 0.9375 mm×0.9375 mm×0.9375 mm (e.g. field-of-view 240 mm×240 mm and image matrix=256×256).

Diffusion Tensor Acquisition: The diffusion-weighted data were acquired using a single-shot spin echo diffusion sensitized echo-planar imaging (EPI) sequence with the balanced Icosa21 encoding scheme (Hasan K M and Narayana P A (2003): Computation of the fractional anisotropy and mean diffusivity maps without tensor decoding and diagonalization: Theoretical analysis and validation. Magn Reson Med. 50:589-598), a diffusion sensitization of b=1000 sec.mm, and a repetition and echo times of TR=6.1 s and TE=84 ms, respectively. EPI image distortion artifacts were reduced by using a SENSE acceleration factor or k-space undersampling of two. The slice thickness was 3 mm with 44 axial slices covering the whole-brain (foramen magnum to vertex), a square field-of-view=240 mm×240 mm, and an image matrix of 256×256 that matched the 2D dual spin echo sequence described above. The number of non-diffusion weighted or b~0 magnitude image averages was 8. Each encoding was repeated twice and magnitude-averaged to enhance the signal-to-noise ratio (SNR); thus, effectively 50 images were acquired for each of the axial sections to cover the whole-brain. The total DTI acquisition time was approximately 7 minutes and resulted in SNR-independent DTI-metric estimation (as described in Hasan K M, Halphen C, Sankar A, Eluvathingal T J, Kramer L, Stuebing K K, Fletcher J M, Ewing-Cobbs L (2007): Diffusion tensor imaging-based tissue segmentation: validation and application to the developing child and adolescent brain. NeuroImage 34:1497-1505).

Conventional MRI Data Processing and Tissue Segmentation: The whole-brain cMRI data were converted into ANALYZE formatted volumes, resliced to isotropic voxels (Ahsan R L, Allom R, Gousias I S, Habib H, Turkheimer F E, Free S, Lemieux L, Myers R, Duncan J S, Brooks, D J, Koepp M J, Hammers A (2007): Volumes, spatial extents and a probabilistic atlas of the human basal ganglia and thalamus. NeuroImage 38:261-270), and skull stripped using the brain extraction tool (BET) of the MRIcro software package.

DTI Data Processing: Although the DTI raw images were acquired with fat suppression, all image volumes were semi-automatically stripped to remove non-parenchymal tissue. Diffusion-weighted data were distortion-corrected using the mutual information maximization approach (Netsch T, Van Muiswinkel A (2004): Quantitative evaluation of image-based distortion correction in diffusion tensor imaging. IEEE-TME 23:789-798). After image distortion correction, the non-diffusion volume was masked using the brain extraction tool. All b0 and diffusion-weighted data were resliced to attain isotropic voxels (as described in Hasan K M, Kamali A, Kramer L A, Papanicolaou A C, Fletcher J M, Ewing-Cobbs L (2008c): Diffusion tensor quantification of the human midsagittal corpus callosum subdivisions across the lifespan. Brain Research 1227:52-67). The diffusion-weighted data were decoded and the diffusion tensor volumes were diagonalized for subsequent quantitative steps. The details of the DTI processing are provided in (as described in Hasan K M, Halphen C, Sankar A, Eluvathingal T J, Kramer L, Stuebing K K, Fletcher J M, Ewing-Cobbs L (2007a): Diffusion tensor imaging-based tissue segmentation: validation and application to the developing child and adolescent brain. NeuroImage 34:1497-1505 and Hasan K M, Kamali A, Kramer L A, Papanicolaou A C, Fletcher J M, Ewing-Cobbs L (2008c): Diffusion tensor quantification of the human midsagittal corpus callosum subdivisions across the lifespan. Brain Research 1227:52-67).

DTI based Tissue Segmentation: All DTI pre- and post-processing stages resulted in ANALYZE volumes. These volumes were subjected to subsequent steps that included tissue segmentation (by the method of Ashburner J, Friston K J (2005). Unified segmentation. NeuroImage 26:839-851), nonlinear registration (by the method of Ashburner J, Friston K (1997): Multimodal image coregistration and partitioning—A unified framework. NeuroImage 6:209-217), spatial normalization (by the methods of Good C D, Johnsrude I S, Ashburner J, Henson R N, Friston K J, Frackowiak R S (2001): A voxel-based morphometric study of ageing in 465 normal adult human brains. NeuroImage 14:21-36; Allen J S, Bruss J, Mehta S, Grabowski T, Brown C K, Damasio H (2008): Effects of spatial transformation on regional brain volume estimates. NeuroImage 42:535-547) and brain atlas labeling (Collins D L, Holmes C, Peters T, Evans A (1995). Automatic 3D Model-Based Neuroanatomical Segmentation. Human Brain Mapping 3:190-208; Collins D L, Zijdenbos, A P, Barré W F C, Evans A C (1999): ANIMAL+INSECT: improved cortical structure segmentation. Proc. of the Annual Symposium on Information Processing in Medical Imaging. In: Kuba, A., Samal, M., Todd-Pokropek, A. (Eds.), vol. 1613 of LNCS. Springer, Berlin, pp. 210-223; Desikan R S, Ségonne F, Fischl B, Quinn B T, Dickerson B C, Blacker D, Buckner R L, Dale A M, Maguire R P, Hyman B T, Albert M S, Killiany R J (2006). An automated labeling system for subdividing the human cerebral cortex on MRI scans into gyral based regions of interest. NeuroImage 31:968-980; Evans A C, Kamber M, Collins D L, MacDonald D (1994): An MRI based probabilistic atlas of neuroanatomy. In: Shorvon S D, Fish D R, Andermann F, Bydder G M, Stefan, H. (Eds.), Magnetic Resonance Scanning and Epilepsy. Plenum, N.Y., pp. 263-274; Hammers A, Koepp M J, Free S L, Brett M, Richardson M P, Labbe C, Cunningham V J, Brooks D J, Duncan J S (2002): Implementation and application of a brain template for multiple volumes of interest. Hum Brain Mapp. 15:165-174; Tzourio-Mazoyer N, Landeau B, Papathanassiou D, Crivello F, Etard O, Delcroix N, (2002). Automated anatomical labeling of activations in SPM using a macroscopic anatomical parcellation of the MNI MRI single subject brain. Neuroimage 15:273-289) implemented in the individual brain atlases using statistical parametric mapping (Alemán-Gómez Y, Melie-García, L, Valdés-Hernandez P (2007): IBASPM: toolbox for automatic parcellation of brain structures. Human Brain Mapping, 12th Annual Meeting; Florence, Italy; Tae W, Kim S, Lee K, Nam E C, Kim K (2008): Validation of hippocampal volumes measured using a manual method and two automated methods (FreeSurfer and IBASPM) in chronic major depressive disorder. Neuroradiology 50:569-581; Tzarouchi L C, Astrakas L G, Xydis V, Zikou A, Kosta P, Drougia A, Andronikou S, Argyropoulou M I (2009): Age-related related grey matter changes in preterm infants: An MRI study. NeuroImage (doi:10.1016/j.neuroimage.2009.03.072) toolbox. All original and modified programs were developed in MATLAB by MATHWORKS based on SPM2 and SPM5 (Wellcome Department of Cognitive Neurology, London, UK).

A pictorial of the main steps used in the atlas-based DTI segmentation procedure is shown in FIG. 11. Using DTI-based clustering the brain was segmented into WM, GM and CSF. The method uses a feature space obtained from a large training set. The contrast in FA (FIG. 11a) maps between CSF, WM, and GM and the cluster separability and discriminability of WM and GM based on the principal diffusivity indices (FIG. 11b). The CSF was segmented based on its high diffusivity and low anisotropy (Cercignani M, Inglese M, Siger-Zajdel M, Filippi, M (2001): Segmenting brain white matter, gray matter and cerebro-spinal fluid using diffusion tensor-MRI derived indices. Magn Reson Imaging 19:1167-1172; Freidlin R Z, Ozarslan E, Komlosh M E, Chang L C, Koay C G, Jones D K, Basser P J (2007): Parsimonious model selection for tissue segmentation and classification applications: a study using simulated and experimental DTI data. IEEE Trans Med Imaging 26(11):1576-1584; Hadjiprocopis A, Rashid W, Toffs P S (2005): Unbiased segmentation of diffusion-weighted magnetic resonance images of the brain using iterative clustering. Magn. Reson. Imaging 23:877-885; Hasan et al., 2007a; Jones D K, Dardis R, Ervine M, Horsfield M A, Jeffree M, Simmons A, Jarosz J, Strong A J (2000): Cluster analysis of diffusion, tensor magnetic resonance images in human head injury. Neurosurgery 47:306-313; Pierpaoli C, Jezzard P, Basser P J, Barnett A, Di Chiro G (1996): Diffusion tensor MR imaging of the human brain. Radiology 201:637-648; Wiegell M R, Tuch D S, Larsson H B, Wedeen V J (2003): Automatic segmentation of thalamic nuclei from diffusion tensor magnetic resonance imaging. NeuroImage 19:391-401). Subsequent steps used the DTI-segmented volumes (FIG. 11c) normalized (FIG. 11d) to the Montreal Neurological Institute (MNI) template (see FIG.

11e) and the international consortium for brain mapping (ICBM) human brain probabilistic atlases (Mazziotta J, Toga A, Evans A, Fox P, Lancaster J (1995): A probabilistic atlas of the human brain: theory and rationale for its development. The International Consortium for Brain Mapping. NeuroImage 2:89-101; Mori S, Oishi K, Jiang H, Jiang L, Li X, Akhter K, Hua K, Faria A V, Mahmood A, Woods R, Toga A W, Pike G B, Neto P R, Evans A, Zhang J, Huang H, Miller M I, van Zijl P, Mazziotta J (2008): Stereotaxic white matter atlas based on diffusion tensor imaging in an ICBM template. NeuroImage 40:570-582; Van Essen D C and Dierker D L (2007): Surface-based and probabilistic atlases of primate cerebral cortex. Neuron 56(2):209-225). The anatomically-labeled brain atlases had a voxel size=1 mm×1 mm×1 mm and matrix=181×217×181. A representative output is shown in FIG. 11f which shows multi-planar views. Qualitative segmentation results on the cortical lobes and subcortical structures were examined using available interactive atlases such as are available from the Structural Informatics Group of the Department of Biological Structure of the University of Washington. Since the segmented volumes (approximately 200 subcortical and cortical regions) were obtained in the DTI native space as labeled volume masks, we were able to obtain directly the corresponding volume-averaged mean values of the corresponding DTI metrics (e.g., FA, mean diffusivity).

Validation of Regional Gray Matter Segmentation Results: For quantitative analyses, we compared the absolute volume obtained using the DTI-based methods with those published previously using manual or automated methods as described by Ahsan R L, Allom R, Gousias I S, Habib H, Turkheimer F E, Free S, Lemieux L, Myers R, Duncan J S, Brooks, D J, Koepp M J, Hammers A, 2007 (Volumes, spatial extents and a probabilistic atlas of the human basal ganglia and thalamus. NeuroImage 38:261-270; Table 5). To reduce the number of comparisons and avoid controversial issues related to laterality (Table 5), we only examined the results of the left putamen. This structure was chosen as a representative deep GM structure since its gender-related developmental and aging trends have been studied extensively using MRI volumetric and DTI region-of-interest or voxel-based methods, as described by Càmara E, Bodammer N, Rodríguez-Fornells A, Tempelmann C (2007) (Age-related water diffusion changes in human brain: a voxel-based approach. NeuroImage 34:1588-1599). All participants were used to examine age trends.

TABLE 5

| Author and year | N(H/S) controls | Age (years) | Delineation methods | Right PUT Vol (mL) | Left PUT Vol (mL) | AI | Age r(p) |
|---|---|---|---|---|---|---|---|
| Ahsan et al., 2007 | 30 | 31 (median) | Rater no. 1 | 4.54 ± 0.63 | 4.61 ± 0.63 | −1.5 | |
| | (15M; 25Rh) | 20-54 | Rater no. 2 | 4.34 ± 0.61 | 4.26 ± 0.50 | 1.9 | |
| | | | Automatic | 6.72 ± 0.64 | 7.03 ± 0.70 | −4.5 | |
| Anastasi et al., 2006 | 35 Rh (21M) | 34 (mean) 22-43 | Automatic (NURBS) | 3.43 ± 0.14 | 3.37 ± 0.19 | 3.4 | |
| Brambilla et al., 2001 | 22 (14M) | 38 ± 10 | Manual | 2.43 ± 0.93 | 3.18 ± 0.92 | −26.7 | −0.33 (0.14) |
| de Jong et al., 2008 | 35 (M) | 65 ± 13 | FSL-FIRST | 6.47 ± 0.86 | 5.90 ± 0.77 | 12.3 | |
| | 35 (F) | 67 ± 12 | (SIENAX) | 5.56 ± 0.75 | 5.24 ± 0.61 | 5.9 | |
| Greenberg et al., 2006 | 138 (38M) | 71 ± 6 60-85 | Automatic GRID | 3.58 ± 0.67 0.32 ± 0.06 | 3.56 ± 0.62 0.32 ± 0.06 | 0.6 | −0.22 −0.37 |
| Gunning-Dixon et al., 1998 | 148 (Rh) | 46.5 ± 17.2 | Manual | 4.36 ± 0.61 | 4.02 ± 0.60 | 8.1 | −0.41 |
| | 82 (W) | 47.4 ± 18.1 (W) | | 4.19 ± 0.53 (W) | 3.88 ± 0.54 (W) | 7.7 | −0.43 |
| | 66 (M) | 45.7 ± 16.5 (M) 18-77 | | 4.56 ± 0.64 (M) | 4.18 ± 0.62 (M) | 8.7 | −0.43 |
| Jacobsen et al., 2001 | 20 (9M) | 35.0 ± 6.8 22-48 | ANALYZE | 4.0 0.291 ± 0.034 | 3.7 0.266 ± 0.030 | 9.0 | −0.40 |
| Jovicich et al., 2009 | 15 | 69.5 ± 4.8 | FreeSurfer | 4.35 ± 0.70 | 4.65 ± 0.85 | −6.6 | |
| | 4 | 34 ± 3 | | 5.64 ± 0.89 | 5.88 ± 0.83 | −4.2 | |
| Keshavan et al., 1998 | 17 (12M) | 22.9 ± 5.1 | Manual | 2.91 ± 0.89 | 2.37 ± 1.13 | 20.5 | |
| Mcdonald et al., 2008 | 21 (10M) | 33.0 ± 10.2 | FreeSurfer ICV-cov | 5.07 ± 0.11 | 5.26 ± 0.11 | −3.7 | |
| Peran et al., 2009 | 30 (16M) | 29.3 ± 5.7 20-41 | FSL-FIRST | 6.66 ± 0.61 | 6.47 ± 0.73 | 2.9 | −0.43 −0.43 |
| Rosas et al., 2001 | 24 (12M) | 41.2 ± 9.8 29-62 | Automatic | 4.5 ± 0.7 | 4.7 ± 0.7 | −4.3 | −0.36 |
| Shattuck et al., 2008 | 40 (20F) | 29.2 ± 6.3 19.3-39.5 | Manual | 4.22 ± 0.49 | 4.25 ± 0.52 | −0.7 | |
| | | | LPBA40/AIR | 5.13 ± 0.61 | 5.17 ± 0.73 | −0.8 | |
| | | | FLIRT | 5.83 ± 0.63 | 5.87 ± 0.69 | −0.7 | |
| | | | SPM5 | 5.77 ± 0.62 | 5.69 ± 0.68 | 1.4 | |
| Vernaleken et al., 2007 | 18 (M) Rh | 35.6 ± 10.4 24-60 | Manual | 4.85 ± 0.56 | 4.64 ± 0.86 | 4.4 | −0.61 −0.43 |

Comparison of DTI Atlas-based segmentation and 3D T1w: the volume results of the 2D DTI-based segmentation with those obtained using the FreeSurfer analysis pipeline on the 3D high resolution T1-weighted data were compared as described in Fischl B, Salat, D H, Busa E, Albert M, Dieterich M, Haselgrove C, van der Kouwe A, Killiany R, Kennedy D, Klaveness S, Montillo A, Makris N, Rosen B, Dale A M, 2002 (Whole brain segmentation: automated labeling of neuroanatomical structures in the human brain. Neuron 33:341-355). A subset of 31 right-handed adolescents and young adults (18 males and 13 females of equivalent age; age range, 15.83-28.83 years) were used for this analysis. The details of the application and validation of FreeSurfer tissue segmentation to cortical and subcortical structures have been described. Since FreeSurfer results were obtained using a high resolution 3D data set that is acquired sagittally, and the DTI-based segmentation results are obtained using 2D axially acquired data set. Therefore, we did not attempt in this work to fuse the results into one common space as this would have required additional non-linear registration and warping procedures that could have biased the results obtained by each analysis pipeline (Allen J S, Bruss J, Mehta S, Grabowski T, Brown C K, Damasio H (2008): Effects of spatial transformation on regional brain volume estimates. NeuroImage 42:535-547; Lancaster J L, Tordesillas-Gutierrez D, Martinez M, Salinas F, Evans A, Zilles K, Mazziotta J C, Fox P T (2007): Bias between MNI and Talairach coordinates analyzed using the ICBM-152 brain template. Hum Brain Mapp. 28(11):1194-205; Shattuck D W, Mirza M, Adisetiyo V, Hojatkashani C, Salamon G, Narr K L, Poldrack R A, Bilder R M, Toga A W (2008): Construction of a 3D probabilistic atlas of human cortical structures. NeuroImage 39:1064-1080). The absolute volumetry results relative and the volume relative to the intracranial volume obtained by each method is reported in the present disclosure Statistical analysis: Group mean comparisons between males and females were made using the t-test for unpaired groups. Within group comparisons were conducted using paired t-tests. Correlations with age were based on the Pearson coefficient (Glantz, 2002). Statistical comparisons between regression coefficients and Bland-Altman bias analysis of methods were conducted as described in Glantz (2002). A p-value <0.05 (two-tailed) was considered statistically significant.

Data Quality and Reproducibility: Since the data from all healthy controls were collected over a 4-year span at high SNR, we collected, using identical protocols a database of water phantom measurements, and adult controls to assure the field uniformity and stability of the MRI scanner. The diffusion encoding (Icosa21b) provided three levels of SNR and hence the SNR dependence of the DTI-metrics and estimates reported herein were considered on all subjects.

RESULTS: The DTI-based segmentation results were validated using the whole brain CSF, WM and GM and on regional structures such as the corpus callosum. Since these examples are more concerned with the GM atlas-based DTI segmentation results, left putamen volume was a representative benchmark to evaluate the accuracy and sensitivity of this approach to age and gender. Age and gender variables were used to test and compare segmentation results.

Comparison of DTI-based and FreeSurfer Results on the Left Putamen Volume: The volume of the left putamen using FreeSurfer was 6.080±0.671 mL, while the DTI-based approach provided 4.815±0.766 mL. The volume of the left putamen obtained using FreeSurfer and the DTI-based approach correlated (r=0.40; p=0.03; N=31; see FIG. 12a).

There was a significant difference between the two approaches (p=1×10−7). A Bland-Altman bias analysis (FIG. 12b) shows that FreeSurfer left putamen volumes are larger than the DTI-based method. The FreeSurfer or T1-weighted intracranial volume (ICV) and 2D-based estimated ICV were not significantly different (e.g. 1559.255±178.421 mL vs. 1569.948±138.596 mL; p=780.715). The left putamen volume-to-ICV percentage (LPUT Vol/ICV*100) was significantly larger using FreeSurfer compared to the DTI-based approach (e.g. 0.392±0.044 vs. 0.308±0.063; p=6×10−10 paired t-test).

Figure 12:
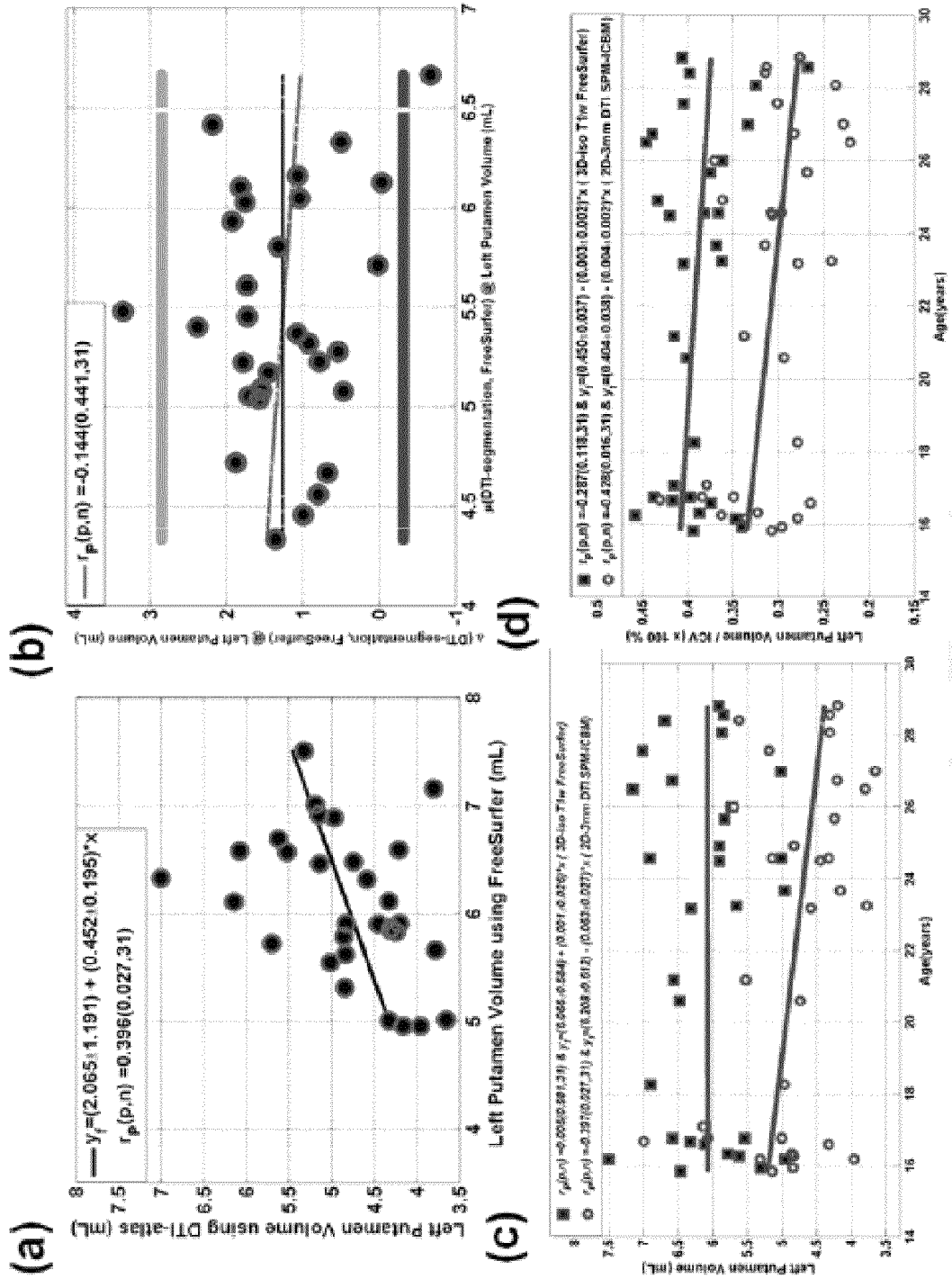
FIG. 12 is the comparison of DTI-segmentation and Free-Surfer volume estimation on the left putamen volume on the N=31 sample. (a) A scatter plot along with the linear regression analysis, (b) a bias analysis using the Bland-Altman method, (c) scatter plots and regression analysis of the dependency of the estimated left putamen volume on age, and (d) scatter plots and regression analysis of the scatter plots and regression analysis of the dependency of the estimated left putamen volume on age.

The sensitivity of the estimated left putamen absolute volume and volume-to-ICV ratio to age is plotted in FIGS. 12c and 12d, respectively. Note that the DTI-segmentation approach predicts that left putamen volume-to-ICV percentage decreases with age (r=−0.43, p=0.02), while FreeSurfer results seem to be less sensitive to age effects (r=−0.29, p=0.12). A further statistical comparison shows that the left putamen annual volume loss rates obtained by FreeSurfer and DTI-segmentation are not statistically different (p=0.54).

DTI-based Left Putamen Normalized Volume and FA Gender and Age Effects: Males had larger intracranial volume (ICY=1607.9±124.2 mL; N=65) as compared to females (ICY=1462.8±115.5 mL; N=71; p<1×10). The DTI-segmented left putamen average volumes were significantly larger in males (5.108±0.811 mL) as compared with females (4.641±0.932 mL; p<1×10$^{-6}$). The left putamen volume-to-ICV percentage was not significantly different between males and females (0.317±0.056 vs. 0.318±0.043; p=0.954).

Figure 13:
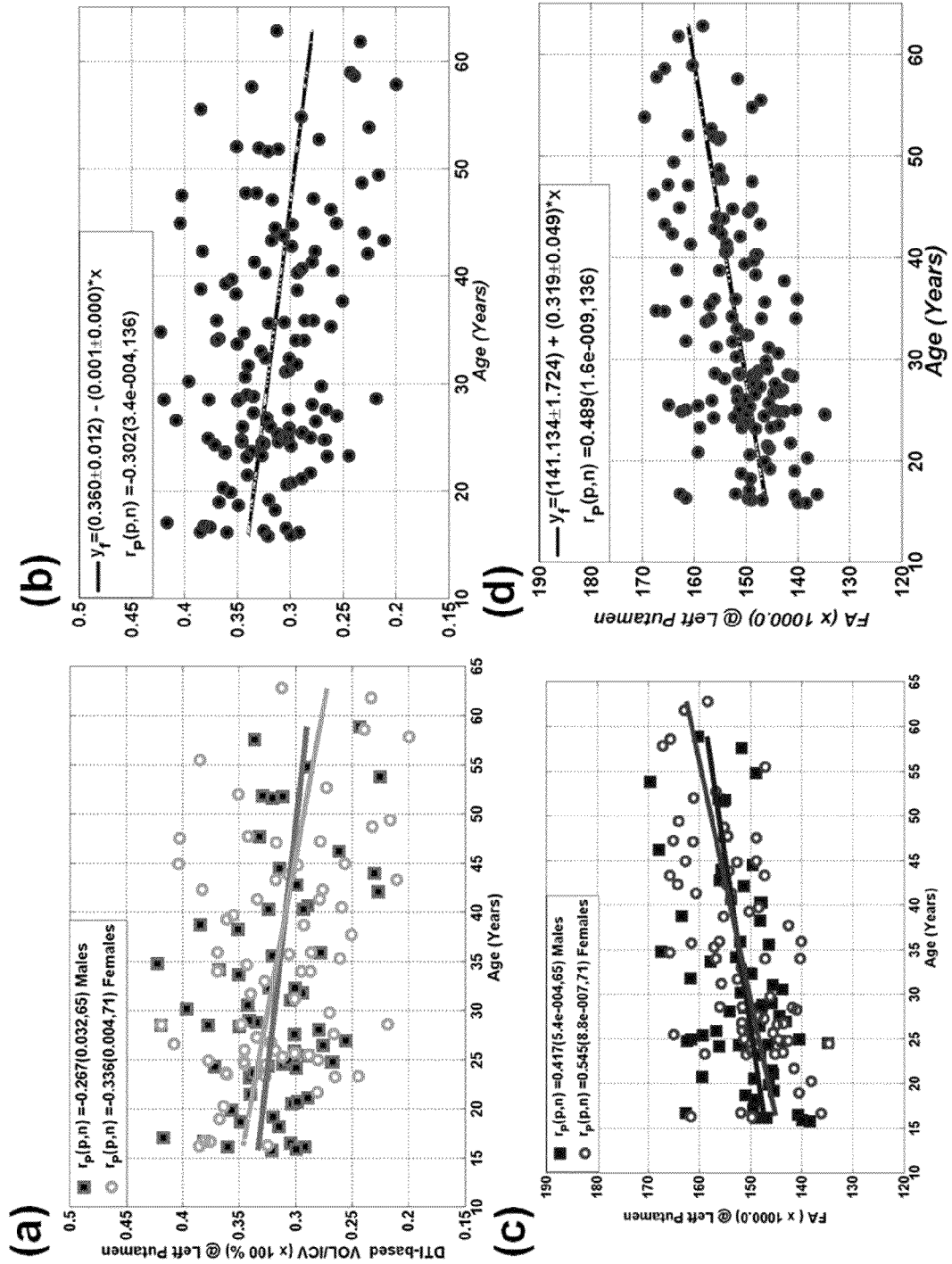
FIG. 13: (a) Scatter plots of the DTI segmentation results of the left putamen volume-to-ICV for (a) both the 65 males and 71 females, (b) the entire cohort (N=136). The average fractional anisotropy values of the left putamen volume is shown in (c) for both males and females and (d) the entire population. Note the gender-independent effects, the decrease in putamen volume and the increase in putamen FA with advancing age.

The left putamen volume-to-ICV percentage and corresponding mean FA values are plotted and compared in FIG. 13a on both males and females and the entire sample (N=136). Note that the putamen volume-to-ICV percentage decreased with advancing age for both males (r=−0.267; p=0.03) and females (r=−0.336; p=0.004; FIG. 13a). The annual putamen volume loss rate did not differ between males and females (p=0.67) and hence males and females were pooled together. FIG. 13b shows that for the entire cross-sectional cohort (N=136), the putamen volume-to-ICV percentage significantly decreased with age (r=−0.3; p=0.0003). FIG. 13c shows that the fractional anisotropy (FA) of the left putamen significantly increased with age in both males (r=0.42; p=0.0005) and females (r=0.55; p<0.000001). The rate of FA increase with age did not differ between males and females (p=0.34). A strong positive correlation between left putamen mean FA and age was found on the entire cohort and is shown in FIG. 13d (r=0.49; p=1.6×10$^{-9}$).

Figure 14:
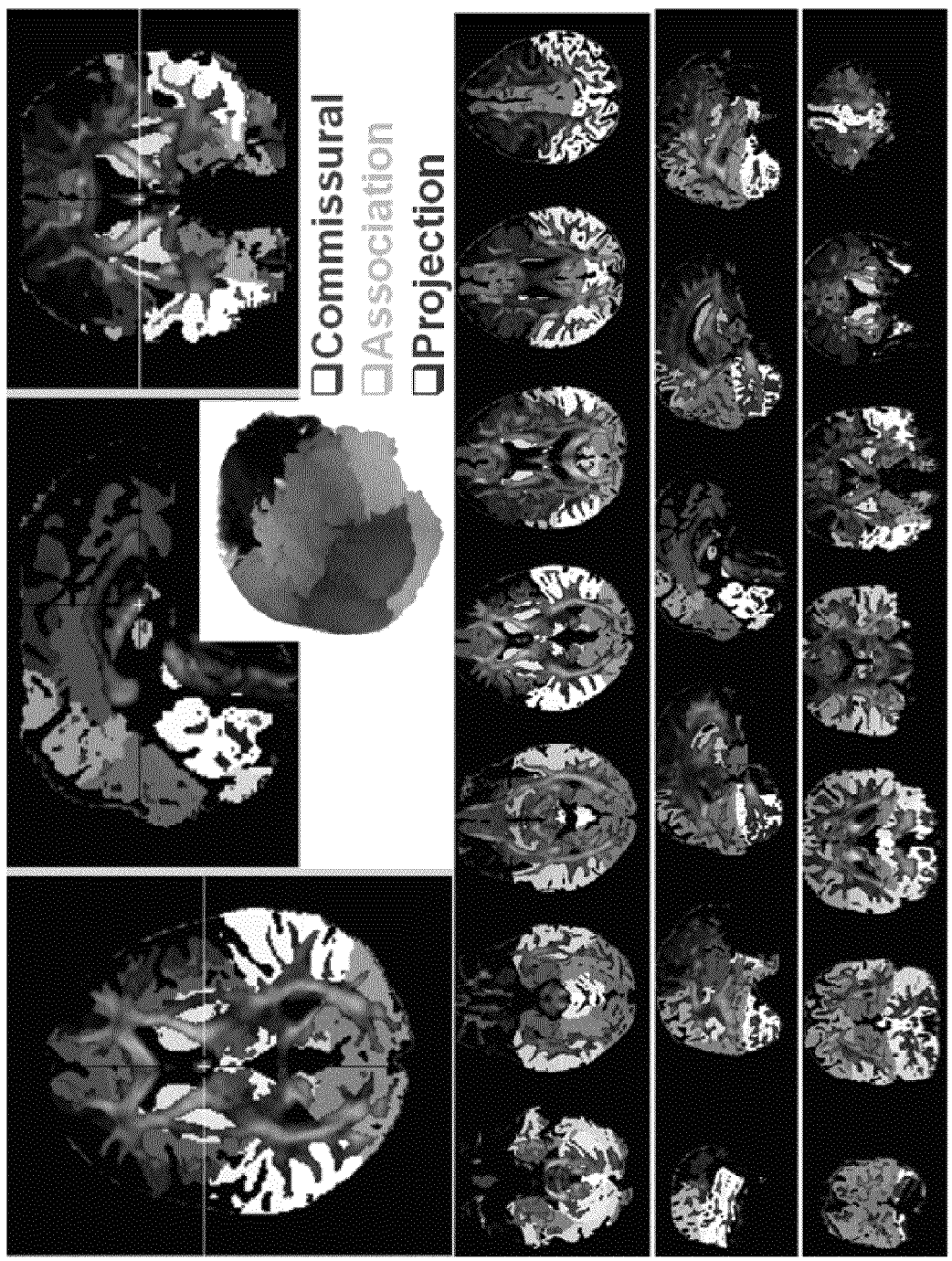
FIG. 14 is an illustration of the application of DTI-based segmentation of gray matter volumes to build a teaching brain digital atlas and to improve the accuracy of quantitative DTI measurements (e.g. fiber tracking, region-of-interest). The figure shows in 3D multi-planar views a fusion of color-coded and FA-modulated principal eigenvector map with the regional gray matter volume segmentation also shown in 3D. The different shades of gray correspond to deep subcortical and lobar regions while red is assigned to commissural fibers oriented right-to-left (e.g. corpus callosum), green is assigned to association fibers oriented anterior-to-posterior (e.g. cingulum) and blue is assigned to projection pathways oriented superior-to-inferior (e.g. corticospinal tract).

Application of the DTI-segmentation: FIG. 14 illustrates an application of the DTI regional segmentation in the DTI native space. The segmented gray matter volumes obtained using this DTI-based approach were fused with the DTI color-coded maps (FA-modulated principal eigenvector) to enhance the accuracy of quantitative DTI measurements using region-of-interest or fiber tracking.

Example 2

The human brain corpus striatum (CS) is composed of the caudate nucleus (CN), putamen (PUT) and globus pallidus (GP) which are three interconnected structures of the basal ganglia. These three structures are involved in several aspects of human cognition and behavior. The degeneration CS has been associated with natural aging, and several pathologies. In addition, the abnormal morphometry of these structures has been used as a marker of several acquired, psychiatric, therapy, and neurodevelopmental conditions. The neuronal mass, dendritic architecture and connectivity of these structures have also been shown to decrease using histological assessment due to natural aging. Since these structures are also known to contain different iron levels, they have been used in MRI literature as benchmarks to model the interplay between MRI intrinsic parameters such as T2 relaxation and diffusion tensor metrics. For the first time using brain atlas-based volumetric methods a comprehensive account of the macro and microstructure of CS on a large healthy cohort across the lifespan has been done.

Figure 15:
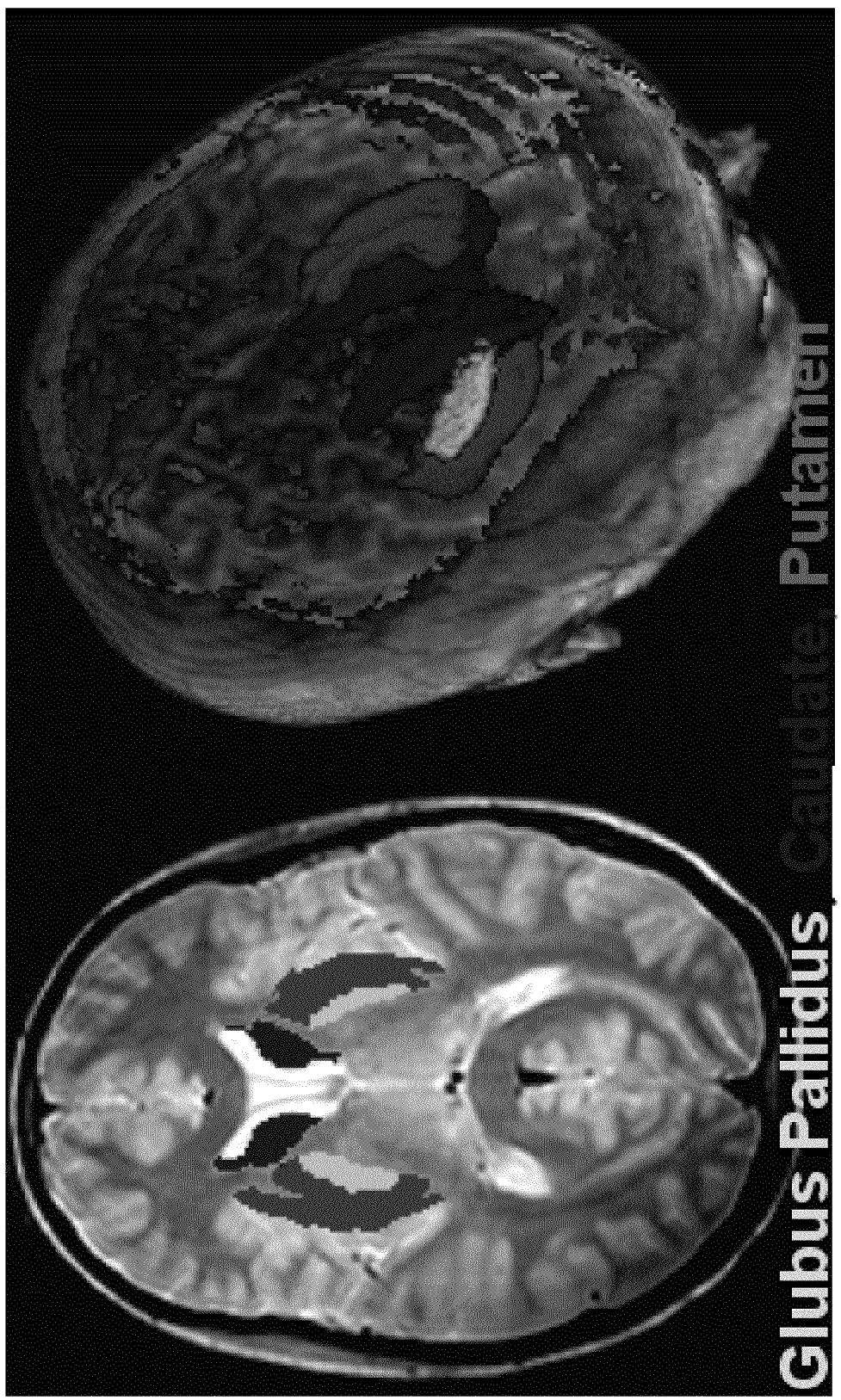
FIG. 15 shows the tissue volume estimated using a brain atlas and DTI-based tissue segmentation approach.

Methods: The participants included 281 healthy children, adolescents, young and older adults aged 6-63 years. The cohort consisted of 147 males (age mean±S.D=31.2±11.5 years), and 134 females (age mean±S.D=34.8±11.7 years). All volunteers were identified as neurologically normal by review of medical history and were medically stable at the time of the assessments. Written informed consent was obtained from the adults, guardians and adolescents and assent from the children Participating in these studies. Conventional and DT-MRI Acquisition: All MRI studies were performed on a 3T Philips Intera scanner with a dual quasar gradient system and an eight channel SENSE-compatible head coil. The MRI protocol included fast dual-echo (TE1/TE2/TR=9/90/6800) for transverse or T2 relaxation mapping and a high resolution (voxel size 0.9375 mm) 3D axially acquired T1-weighted spoiled gradient sequence. The DTI data were acquired using a single-shot spin-echo diffusion sensitized EPI sequence, b=1000 sec mm−2, TR/TE=6100/84 msec. The slice thickness was 3.0 mm with 44 contiguous axial slices covering the entire brain; FOV=240×240 mm2 and matching the dual echo sequence. The number of b=0 images was 8; in addition each diffusion encoding was repeated twice and magnitude averaged to enhance signal-to-noise ratio. Tissue Volume was estimated (FIG. 15) using a brain atlas and DTI-based tissue segmentation approach. The DTI-based method for volume estimation was also compared with FreeSurfer applied on the 3D T1-weighted volumes.

Data Processing and Statistical Analyses: The intracranial-volume (ICV) normalized volumes, and corresponding T2 relaxation and DTI metrics (e.g., fractional anisotropy=FA; radial diffusivity=$\lambda_\perp$; axial diffusivity=$\lambda_\parallel$)) were computed and modeled for both males and females as $y_i=\beta_0+\beta_1*age+\beta_2*age^2$, then the general least-squares were used to compute the coefficients, standard errors and their significance using analysis-of-variance methods as detailed in Hasan K M, Sankar A, Halphen C, Kramer L A, Brandt M E, Juranek J, Cirino P T, Fletcher J M, Papanicolaou A C, Ewing-Cobbs L, 2007b (Development and organization of the human brain tissue compartments across the lifespan using diffusion tensor imaging. Neuroreport 18:1735-1739).

Figure 16:
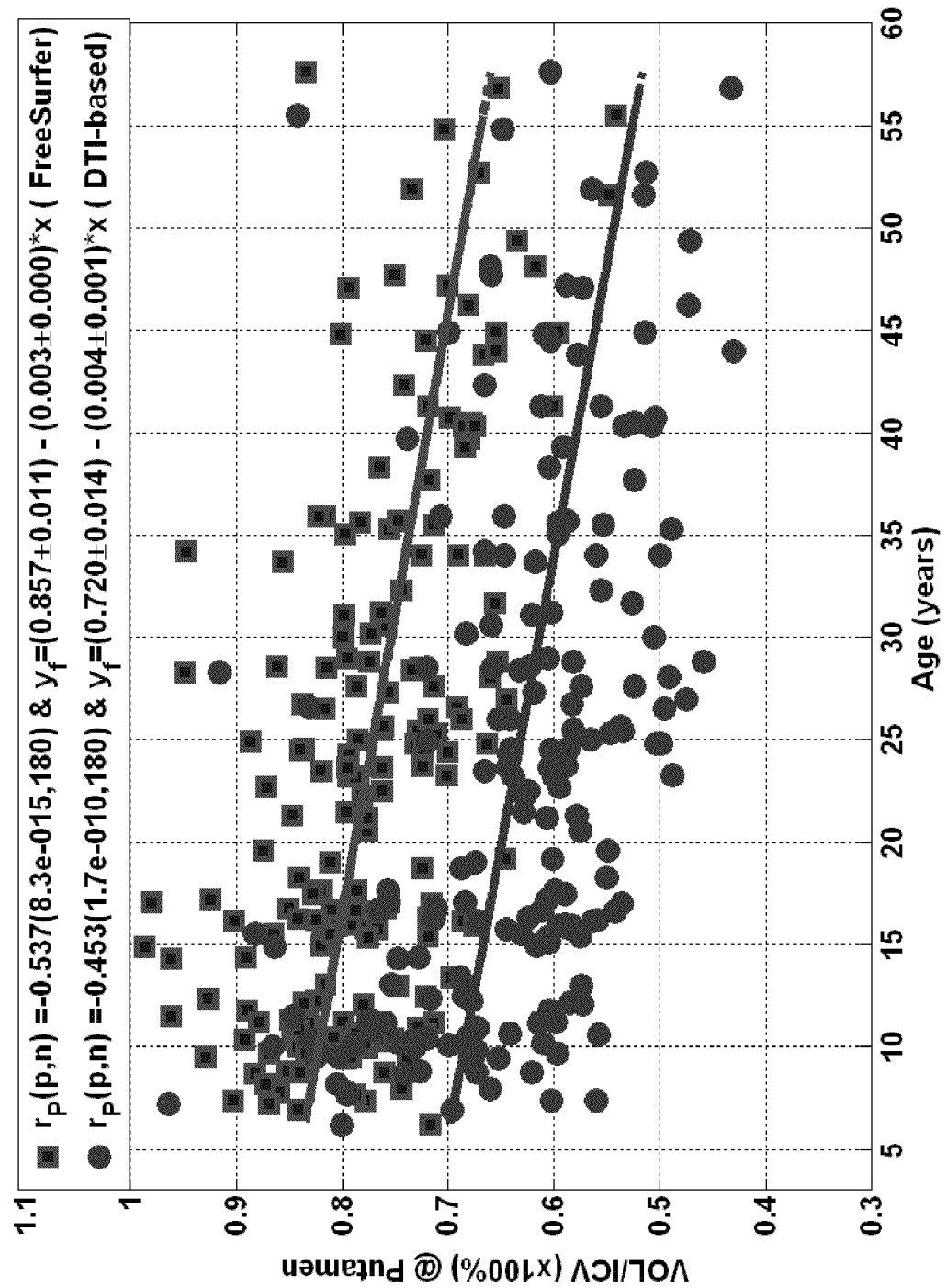
FIG. 16 shows the predicted side- and gender-independent loss of putamen volume.
Figure 17:
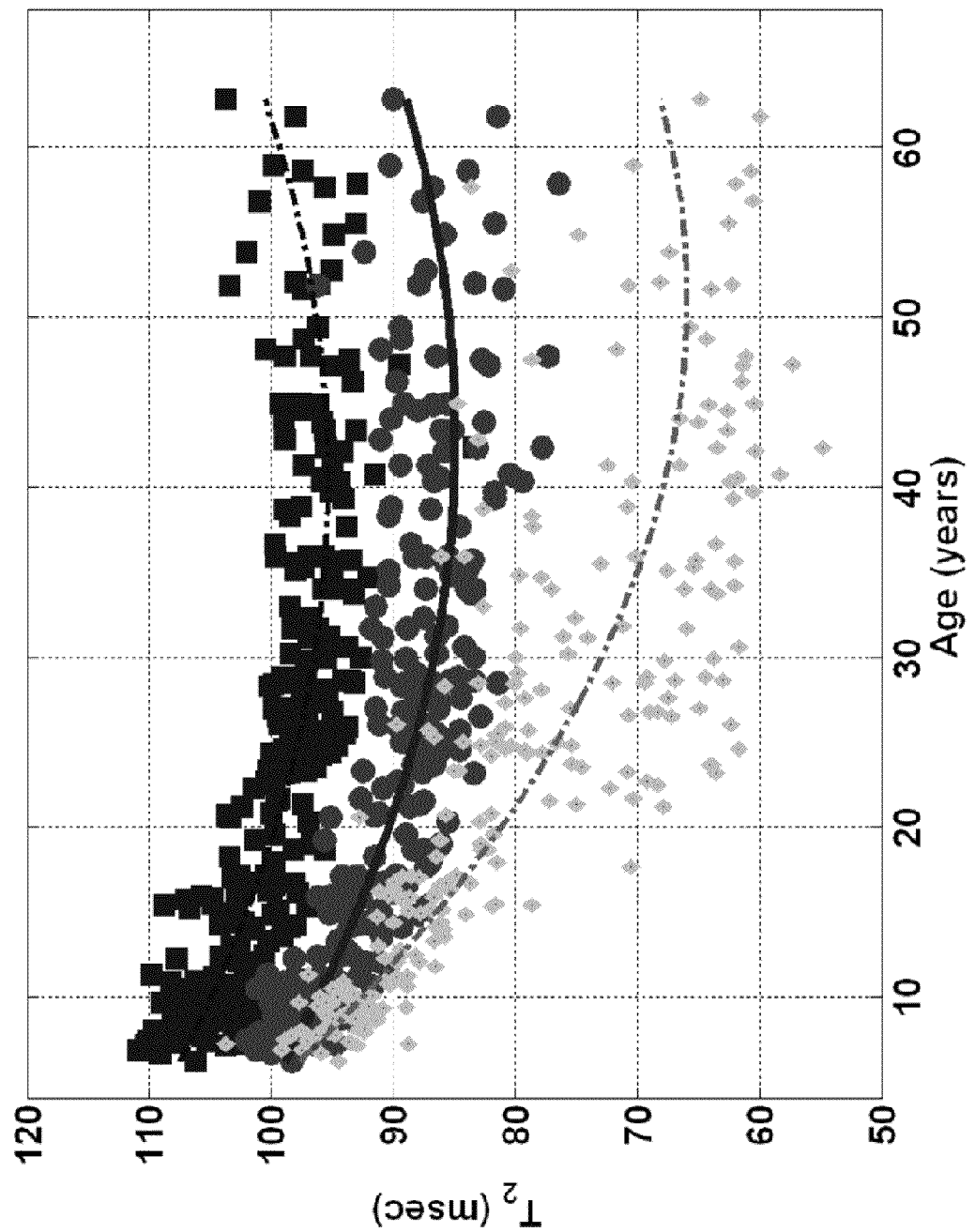
FIGS. 17, 18, and 19 show, respectively, the lifespan mean T2, mean diffusivity (MD), and fractional anisotropy (FA) trajectories for the caudate nucleus (CN), putamen (PUT) and globus pallidus (GP).
Figure 18:
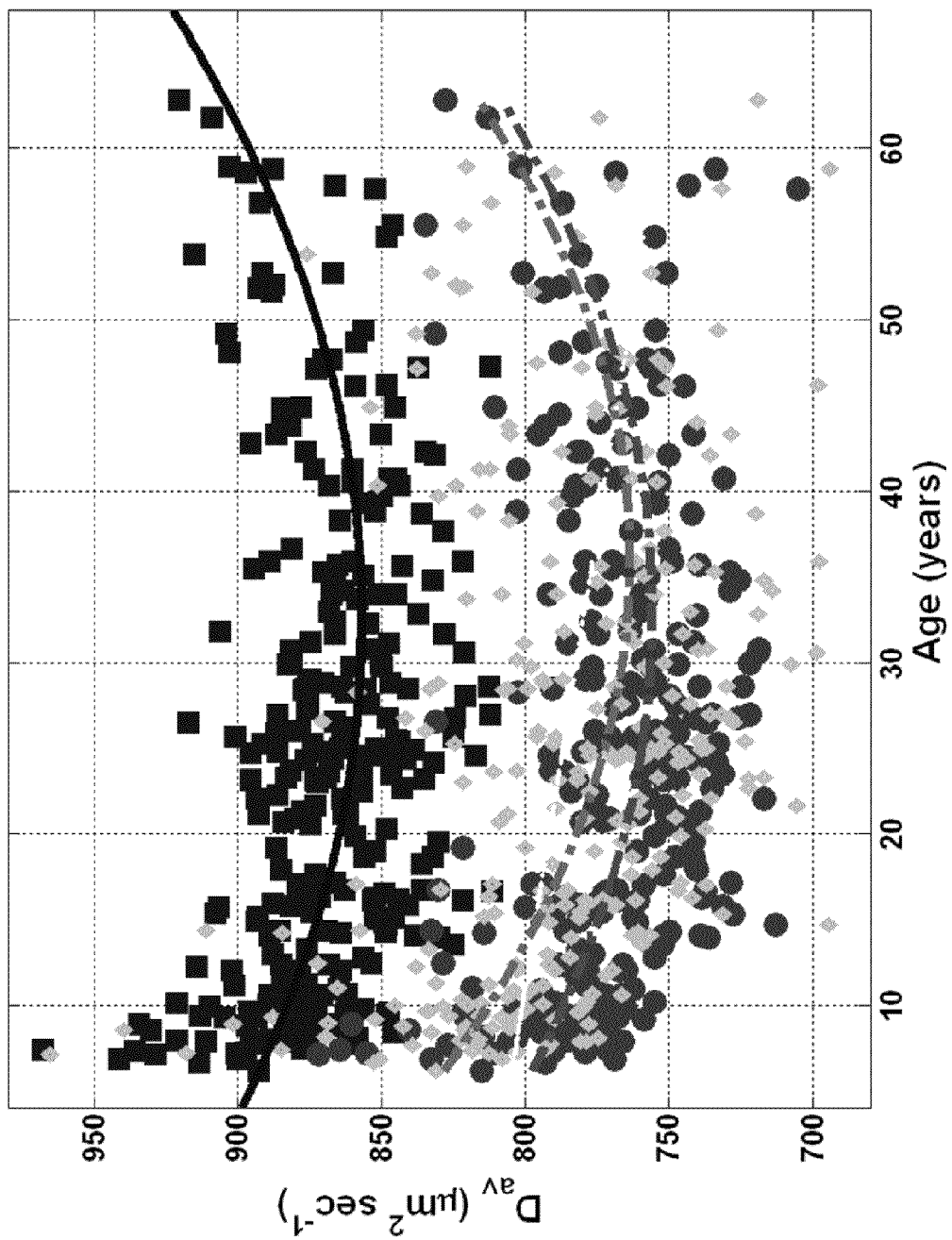
Figure 19:
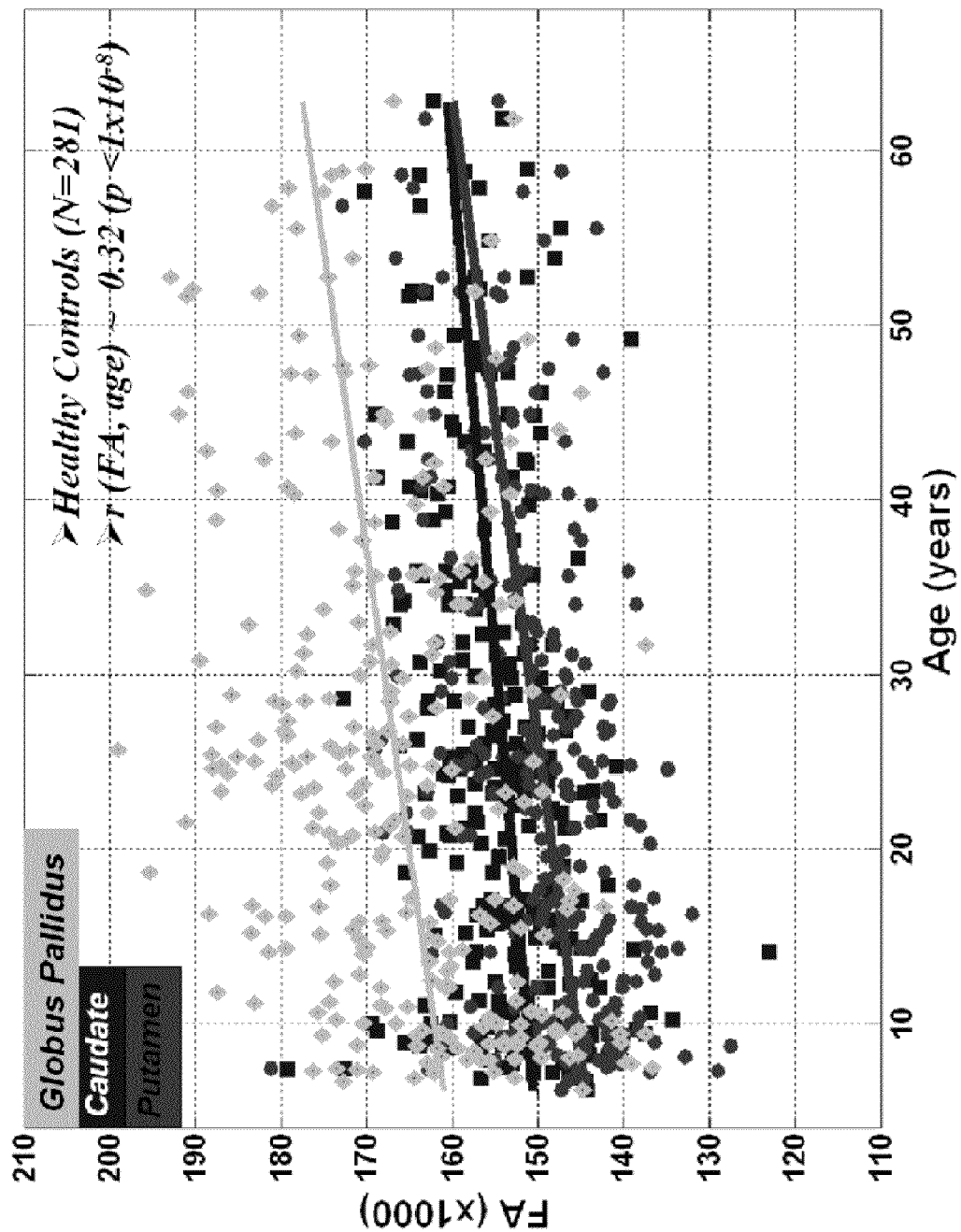

Results: To demonstrate the validity of the segmentation approach used in this work to obtain estimates of volume, T2 and DTI metrics, we plotted the normalized volume age trajectories obtained using both the DTI method and FreeSurfer on a subset of 180 controls. Both DTI and FreeSurfer predicted a side- and gender-independent loss of caudate, putamen and globus pallidus volume (see FIG. 16 for the putamen). The lifespan mean T2, Mean diffusivity and FA trajectories for the CN, PUT and GP are shown in FIGS. 17, 18, and 19, respectively. Note the linear age-dependence and the statistically significant ($p<0.001$) anisotropy spatial heterogeneity trend FA(GP)>FA(CN)>FA(PUT). Note also that T2(CN)>T2(PUT)>T2(GP) at all ages. The mean diffusivity and T2 relaxation follow quadratic curves across the lifespan. The peak at minimum mean diffusivity is attained ~33 years, whereas the T2 relaxation minimum is attained at ~43 years reflecting that diffusion and relaxation mechanisms may have unique neuronal mechanisms.

This is the largest cross-sectional study that reports simultaneous measurements of volume, and corresponding T2 relaxation and DTI metrics to elucidate the interplay between MRI macro and microstructural attributes of deep basal tissue. Validated atlas-based T1w, DTI, and T2w methods were for tissue segmentation. The steady decrease in CN, PUT and GP volume with age is consistent with histological. The results on the volume loss are also consistent with MRI-volumetry studies that reported subcortical and frontostriatal connectivity loss, but some inconsistencies need to be noted in published literature.

The loss in CN, PUT and GP volume may relate to the degradation in cognitive and motor skills in healthy aging. The decrease in T2 with age has been attributed to iron accumulation. The rise in T2 in the mid forties seems to reduce the sensitivity and specificity of this metric to iron as a result of increased extracellular water. This hypothesis is substantiated by the observed commensurate increase in mean diffusivity which seems to be earlier and more sensitive predictor tissue integrity than T2. The steady increase in caudate and putamen FA observed across the lifespan is consistent with previous reports. The increase in FA may not be explained by partial volume averaging as an increase in mean diffusivity due to CSF (e.g. ventricular enlargement) would have decreased FA. Note that iron accumulation may not be the main contributor to the increase in FA as putaminal iron concentration is expected to be larger than that in CN. The increase in anisotropy may be a result of the loss of dendrites and connections between these structures, frontal lobe, thalamus and deeper structures such as the substantia nigra. This demonstrates that these deep gray matter and iron rich structures may be used as benchmarks or surrogate neuroimaging markers to test and model the neuronal contributors to tissue volume loss in both health and disease.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method for studying microstructural integrity or connectivity or both of a region of interest (ROI) in a patient comprising:
   acquiring, via an imaging system, diffusion magnetic resonance (MRI) data in said ROI by using Icosahedral Diffusion Tensor Encoding Scheme (IDTES);
   computing, via the imaging system, mean diffusivity (MD) and fractional anisotropy (FA) by using logarithm-moment algorithm (LMA); and displaying, on a display, the microstructural integrity or connectivity or both of ROI based on the computed MD and FA; wherein values of MD and FA are indicative of the microstructural integrity or connectivity of the ROI.

2. The method of claim 1, wherein the diffusion MRI data comprises diffusion-weighted imaging (DWI) data or diffusion tensor imaging (DTI) data.

3. The method of claim 1, wherein displaying the microstructural integrity or connectivity or both of ROI takes place in real time.

4. The method of claim 1, further comprising:
generating a training set of said ROI to obtain MD and FA thresholds; and
segmenting tissue in said ROI based on the computed MD and FA and said thresholds.

5. The method of claim 4, further comprising:
obtaining an atlas comprising said ROI; and
registering said segmented tissue with said atlas.

6. The method of claim 5, wherein registering said segmented tissue with said atlas takes place in real time.

7. An imaging system configured for studying microstructural integrity or connectivity or both of a region of interest (ROI) in a patient, containing software that, when executed by a processor, causes the processor to:
acquire diffusion magnetic resonance (MRI) data in said ROI by using an Icosahedral Diffusion Tensor Encoding Scheme (IDTES);
compute mean diffusivity (MD) and fractional anisotropy (FA) by using a logarithm-moment algorithm (LMA); and
display the microstructural integrity or connectivity or both of said ROI based on the computed MD and FA; wherein values of MD and FA are indicative of the microstructural integrity or connectivity of the ROI.

8. The imaging system of claim 7, wherein said software causes the processor to display the microstructural integrity or connectivity or both of said ROI based on the computed MD and FA in real time.

9. The imaging system of claim 7 wherein said software further causes the processor to
generate a training set to obtain MD and FA thresholds; and
segment tissue in said ROI based on the computed MD and FA and said thresholds.

10. The imaging system of claim 9 wherein said software further causes the processor to
obtain an atlas comprising said ROI; and
register said segmented tissue with said atlas.

11. A method for segmenting tissue in a region of interest (ROI) in a patient comprising:
obtaining, via a computer system, diffusion magnetic resonance (MRI) data in said ROI;
computing, via the computer system, mean diffusivity (MD) and fractional anisotropy (FA) from said diffusion MRI data;
generating, via the computer system, a training set of said ROI to obtain MD and FA thresholds;
segmenting, via the computer system, tissue in said ROI based on the computed MD and FA and said thresholds; and
providing the segmented tissue for use in determining parameters of the ROI or imaging of the ROI.

12. The method of claim 11, wherein the diffusion MRI data comprises diffusion-weighted imaging (DWI) data or diffusion tensor imaging (DTI) data.

13. The method of claim 11, wherein tissue in said ROI comprises gray matter (GM), white matter (WM), or cerebrospinal fluid (CSF).

14. The method of claim 11 further comprising:
obtaining an atlas comprising said ROI; and
registering said segmented tissue with said atlas.

15. The method of claim 14, wherein the computing, generating, segmenting, obtaining an atlas, and registering take place in real time while said diffusion MRI data are being obtained or after said diffusion MRI data have been obtained.

16. The method of claim 11, wherein the computing, generating, and segmenting take place in real time while said diffusion MRI data are being obtained or after said diffusion MRI data have been obtained.

17. A non-transitory computer-readable storage medium (CRSM) containing software that, when executed by a processor, causes the processor to:
obtain diffusion magnetic resonance (MRI) data in a region of interest (ROI) in a patient;
compute mean diffusivity (MD) and fractional anisotropy (FA) from said diffusion MRI data;
generate a training set of said ROI to obtain MD and FA thresholds;
segment tissue in said ROI based on the computed MD and FA and said thresholds; and
provide the segmented issue for use in determining parameters of the ROI or imaging of the ROI.

18. The CRSM of claim 17 wherein said software further causes the processor to
obtain an atlas comprising said ROI; and
register said segmented tissue with said atlas.

19. A method comprising
acquiring, via an imaging system, diffusion magnetic resonance (MRI) data in a region of interest (ROI) in a patient by using an Icosahedral Diffusion Tensor Encoding Scheme (IDTES);
computing, via the imaging system, mean diffusivity (MD) and fractional anisotropy (FA) by using a logarithm-moment algorithm (LMA);
generating, via the imaging system, a training set of said ROI to obtain MD and FA thresholds;
segmenting, via the imaging system, tissue in said ROI based on the computed MD and FA and said thresholds;
obtaining, via the imaging system, an atlas comprising said ROI;
registering, via the imaging system, said segmented tissue with said atlas; and
providing the segmented tissue for use in determining parameters of the ROI or imaging of the ROI.

20. A non-transitory computer-readable storage medium (CRSM) containing software that, when executed by a processor, causes the processor to
acquire diffusion magnetic resonance (MRI) data in a region of interest (ROI) in a patient by using an Icosahedral Diffusion Tensor Encoding Scheme (IDTES);
compute mean diffusivity (MD) and fractional anisotropy (FA) by using a logarithm-moment algorithm (LMA);
generate a training set of said ROI to obtain MD and FA thresholds;
segment tissue in said ROI based on the computed MD and FA and said thresholds;
obtain an atlas comprising said ROI;
register said segmented tissue with said atlas; and
provide the segmented tissue for use in determining parameters of the ROI or imaging of the ROI.

* * * * *